(12) United States Patent
Coleman et al.

(10) Patent No.: US 10,947,211 B2
(45) Date of Patent: Mar. 16, 2021

(54) PROCESS FOR THE PREPARATION OF GLYCEROL CARBONATE

(71) Applicants: Fergal Coleman, Antrim (GB); Sophie Tyrrell, Antrim (GB); Martin Philip Atkins, Antrim (GB); Albert Ferrer Ugalde, Antrim (GB); Ignazio Scarlata, Antrim (GB); Yoan Delavoux, Antrim (GB)

(72) Inventors: Fergal Coleman, Antrim (GB); Sophie Tyrrell, Antrim (GB); Martin Philip Atkins, Antrim (GB); Albert Ferrer Ugalde, Antrim (GB); Ignazio Scarlata, Antrim (GB); Yoan Delavoux, Antrim (GB)

(73) Assignee: The Queen's University of Belfast, Belfast (GB)

(*) Notice: Subject to any disclaimer, the term of this patent is extended or adjusted under 35 U.S.C. 154(b) by 0 days.

(21) Appl. No.: 16/071,745

(22) PCT Filed: Jan. 20, 2017

(86) PCT No.: PCT/GB2017/050151
§ 371 (c)(1),
(2) Date: Jul. 20, 2018

(87) PCT Pub. No.: WO2017/125759
PCT Pub. Date: Jul. 27, 2017

(65) Prior Publication Data
US 2019/0292164 A1    Sep. 26, 2019

(30) Foreign Application Priority Data
Jan. 20, 2016 (GB) ...................... 1601057

(51) Int. Cl.
*C07D 317/36* (2006.01)
*B01J 31/02* (2006.01)
*C07C 68/065* (2020.01)

(52) U.S. Cl.
CPC ........ *C07D 317/36* (2013.01); *B01J 31/0237* (2013.01); *B01J 31/0287* (2013.01); *C07C 68/065* (2013.01)

(58) Field of Classification Search
CPC .................................................. C07C 68/065
See application file for complete search history.

(56) References Cited

U.S. PATENT DOCUMENTS 2,915,529 A   12/1959   Bell, Jr. et al.
2014/0235875 A1   8/2014   Hatti-Kaul et al.

FOREIGN PATENT DOCUMENTS

| CN | 101717338 A1 | 6/2010 |
| CN | 103467435 A | 12/2013 |
| CN | 103030622 B1 | 4/2014 |
| CN | 105709785 A | 6/2016 |
| WO | 2015019108 A1 | 2/2015 |

OTHER PUBLICATIONS

Ochoa-Gomez, Jose., et al. "Synthesis of glycerol 1,2-carbonate by transesterification of glycerol with dimethyl carbonate using trimethylamine as a facile separable homogenous catalyst." Green Chemistry. (2012), vol. 14, pp. 3368-3376. (Year: 2012).*
Rokicki, G., et al. "Hyperbranched aliphatic polyethers obtained from environmentally benign monomer: glycerol carbonate." Green Chem. (2005), vol. 7, pp. 529-539. (Year: 2005).*
Ochoa-Gomez, Jose., et al. "Synthesis of glycerol 1,2-carbonate by transesterification of glycerol with dimethyl carbonate using triethylamine as a facile separable homogenous catalyst." Green Chemistry. (2012), vol. 14, pp. 3368-3376. (Year: 2012).*
International Search Report dated May 26, 2017.
Leon-Reina Laura et al.: "Structural and Surface Study of Calcium Glyceroxide, an Active Phase for Biodiesel Production Under Hetergeneous Catalysis", Journal of Catalysis, Academic Press, Duluth, MN, US, vol. 300, Jan. 31, 2013, pp. 30-36.
Huanjun Wang et al: "Production of Glycerol Carbonate via Reactive Distillation and Extractive Distillation: An Experimental Study"; Chinese Journal of Chemical Engineering, vol. 23, No. 9, Sep. 1, 2015, pp. 1469-1474.
Ochoa-Gomez J R et al.: "Synthesis of Glycerol Carbonate from Blycerol and Dimethyl Carbonate by Transesterification: Catalyst Screening and Reaction Optimization"; Applied Catalysis A: General, Elsevier, Amsterdam, NL, vol. 366, No. 2, Sep. 25, 2009, pp. 315-324.
GB Search Report dated Nov. 28, 2016.
Huajun Wang et al: "Production of Glycerol Carbonate via Reactive Distillation and Extractive Distillation: An Experimental Study"; Chinese Journal of Chemical Engineering, vol. 23, No. 9, Sep. 1, 2015, pp. 1469-1474.

* cited by examiner

*Primary Examiner* — John S Kenyon
(74) *Attorney, Agent, or Firm* — Ryan T. Grace; Advent, LLP

(57) ABSTRACT

This invention relates to a process for the preparation of glycerol carbonate from the reaction of glycerol and a dialkylcarbonate, for example dimethyl carbonate, or a cyclic alkylene carbonate. More specifically, the invention relates to a process where the synthesis of glycerol carbonate is conducted in the presence of a homogeneous transesterification catalyst and involves the partial reaction of a glycerol reactant stream and a dialkyl carbonate or cyclic alkylene carbonate reactant stream and an intermediate step of alcohol by-product separation before further reaction in order to improve glycerol conversion and glycerol carbonate selectivity and yield.

20 Claims, 4 Drawing Sheets

PROCESS FOR THE PREPARATION OF GLYCEROL CARBONATE

Figure 1:
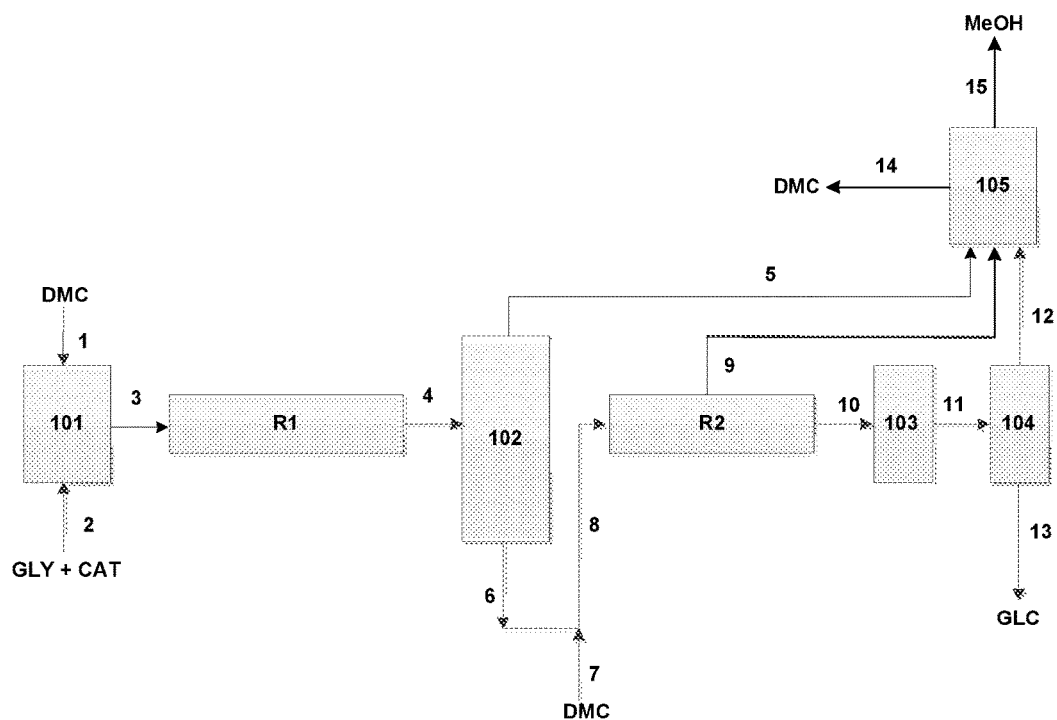

This invention relates to a process for the preparation of glycerol carbonate from the reaction of glycerol and a dialkyl carbonate, for example dimethyl carbonate, or a cyclic alkylene carbonate. More specifically, the invention relates to a process where the synthesis of glycerol carbonate is conducted in the presence of a homogeneous transesterification catalyst and involves the partial reaction of a glycerol reactant stream and a dialkyl carbonate or cyclic alkylene carbonate reactant stream and an intermediate step of alcohol by-product separation before further reaction in order to improve glycerol conversion and glycerol carbonate selectivity and yield.

Glycerol carbonate is a stable, colourless liquid that has found use as a solvent, detergent, electrolyte component, curing agent and blowing agent, as well as a chemical intermediate for the preparation of surfactants and polymers. In particular, glycerol carbonate is known to be a precursor to the formation of glycidol, which is a compound which has a number of valuable industrial uses. For instance, glycidol is known to have properties making it useful in stabilizers, plastics modifiers, surfactants, gelation agents and sterilizing agents. Furthermore, glycidol is known to be useful as an intermediate in the synthesis of glycidyl ethers, esters, amines, as well as glycidyl carbamate resins and polyurethanes. Glycidol has therefore found application in a variety of industrial fields including textile, plastic, pharmaceutical, cosmetic and photochemical industries.

Known commercial processes for the preparation of glycidol include epoxidation of allyl alcohol using hydrogen peroxide and a tungsten-oxide based catalyst, and the reaction of epichlorohydrin with bases. However, there are drawbacks relating to these processes. For instance, the epoxidation of allyl alcohol involves several process steps and suffers problems relating to decomposition of the catalyst. Meanwhile, the high cost of raw materials and/or the management of waste by-products are a concern in both cases.

Glycerol is produced in large quantities as a by-product in the production of biodiesels. With an increasing focus on the use of biofuels to at least partly replace petroleum fuels, the production of glycerol has increased to levels far higher than current demand. As a result, glycerol is a cheap and readily available material, particularly in countries where production of biofuels is prevalent, and there has been an increased focus on the development of suitable applications of glycerol. There are several known glycerol-based routes to the formation of glycerol carbonate. These include direct carbonylation reactions with carbon monoxide or carbon dioxide. However, from a thermodynamic stand-point, direct carbonylation using carbon dioxide is unfavourable and only poor conversion yields have been reported to date. Carbonylation of glycerol with CO in the presence of oxygen and a Cu or Pd catalyst has been reported in good yields. However, handling of toxic carbon monoxide on an industrial scale can be problematic and costly.

Reaction of glycerol with urea is another known method for producing glycerol carbonate, typically involving use of catalysts with Lewis acidic sites, such as Zn, Al and Zr based species. However, the release of large quantities of ammonia by-product, the high temperatures required and poor recyclability of catalysts have limited the industrial application of this method.

Transesterification of dialkylcarbonates, including cyclic carbonates, with glycerol has been used as means for generating glycerol carbonate. Transesterification of dialkyl carbonates, for example dimethyl carbonate, with glycerol is a reversible reaction. Furthermore, the primary alcohol group of glycerol carbonate can react with a further equivalent of dimethyl carbonate to produce glycerol dicarbonate (GDC), which can further react to form diglycerol tricarbonate (GTC). Meanwhile, methanol which is produced as a by-product during the reaction can react with glycerol carbonate to regenerate glycerol and dimethyl carbonate (i.e. the reverse reaction).

U.S. Pat. No. 8,314,259 relates to a method of manufacturing glycerol carbonate from glycerol and dimethyl carbonate which utilises a lipase bio-catalyst. U.S. Pat. No. 8,314,259 states that the lipase catalysed reaction may be performed in the presence of molecular sieves which function to remove methanol by-product, and are said to drive the forward reaction in terms of chemical equilibria. When molecular sieves are used, conversion and yield do not, however, appear to exceed 80% in the method of U.S. Pat. No. 8,314,259, even after reaction times of 25 hours, as illustrated in FIGS. 4 to 6 thereof.

US 2014/0235875 relates to a method for the formation of cyclic carbonates from the reaction of a polyol, such as trimethylolpropane, and a dialkyl carbonate wherein adsorbents such as molecular sieves are used in place of a catalyst. The adsorbent adsorbs alcohol by-product formed during the reaction, which is said to increase the selectivity of the reaction. The maximum selectivity for the cyclic carbonate reported in the examples of US 2014/0235875 where a polyol is reacted with dimethyl carbonate in the presence of molecular sieves appears to be 93.6% (Run 4 of Table 3). However, conversion is ostensibly low in that example, since 23.1% of the product mixture was unreacted polyol.

The use of heterogeneous adsorbents such as molecular sieves are not typically associated with processes capable of continuous operation and regeneration of the adsorbent and/or separation of adsorbed material from the adsorbent can be both energy and labour intensive. In particular, it will be appreciated that for every mole of glycerol carbonate formed during the reaction of glycerol and dimethyl carbonate, two moles of methanol by-product is formed. As such, very sizeable adsorber beds relative to product volume would be required in these processes, making scale-up more difficult.

Rokicki et al., Green Chem., 2005, 7, pages 529 to 539 (hereinafter referred to as "Rokicki et al") primarily relates to the formation of hyperbranched aliphatic polyethers from glycerol carbonate by means of anionic polymerisation. However, Rokicki et al also describes a suitable method for preparing the glycerol carbonate precursor under mild conditions. Dimethyl carbonate was used in a molar excess (3:1) with respect to glycerol in order to shift the reaction equilibrium towards the product. It is reported that, when glycerol containing less than 2% water was used as the starting material and when the reaction was carried out at 60 to 70° C. and in the presence of $K_2CO_3$ catalyst, glycerol carbonate was obtained in almost quantitative yield. The reaction is said to be performed under reflux for three hours before methanol by-product is distilled off at the end of the reaction, along with unreacted dimethyl carbonate.

Rokicki et al also describes how the use of larger (10-fold) excess of dimethyl carbonate led to the formation of diglycerol tricarbonate. Meanwhile, a large excess of dimethyl carbonate, a reaction temperature of above 90° C. and progressive methanol removal from the reaction system led preferentially to the formation of glycerol dicarbonate (see page 530, right hand column and Scheme 1 of Rokicki et al).

There remains a need for a process for the production of glycerol carbonate which process benefits from both high conversion and high selectivity and can be operated as part of a continuous process. The present invention is based on the surprising discovery that the preparation of glycerol carbonate from the reaction of glycerol with a dialkyl carbonate or a cyclic alkylene carbonate may be improved by an intermediate step of by-product alcohol separation. Specifically, where a homogeneous transesterification catalyst is used, an intermediate step of by-product alcohol separation can improve the total conversion and yield of glycerol carbonate. In addition, it has also been found that selectivity for glycerol carbonate can be increased even further if, following the intermediate alcohol separation step, the further reaction is accompanied by continuous alcohol by-product removal.

The present invention is also based on the finding that specifically selected homogeneous transesterification catalysts are particularly useful for maximising conversion and yield of glycerol carbonate in the process.

In a first aspect, the present invention provides a process for preparing glycerol carbonate comprising the steps of:

(i) contacting and partially reacting a glycerol reactant stream with: a) a dialkyl carbonate reactant stream, comprising greater than 80 wt. % dialkyl carbonate; and/or b) a cyclic alkylene carbonate reactant stream, comprising greater than 80 wt. % cyclic alkylene carbonate, in a first reaction zone in the presence of a homogeneous transesterification catalyst;

(ii) separating at least a portion of the alcohol by-product formed from the reaction of dialkyl carbonate and/or cyclic alkylene carbonate with glycerol in step (i) from the reaction mixture so as to obtain an alcohol-containing by-product stream;

(iii) reacting at least a portion of the remaining reactants in a second reaction zone in the presence of the homogeneous transesterification catalyst; and (iv) obtaining a glycerol carbonate product stream.

The process of the present invention involves a transesterification reaction between glycerol and dialkyl carbonate or cyclic alkylene carbonate, leading to the formation of glycerol carbonate and alcohol by-product, as illustrated below in Schemes 1 and 2.

Scheme 1

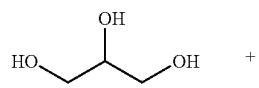

In this aspect of the invention, it has been found to be advantageous to initially allow the build-up of by-product alcohol following reaction of the reactant streams in step (i) and prior to an intermediate by-product alcohol removal step (ii). Glycerol and dialkyl carbonate streams are not normally miscible, resulting in a biphasic reaction mixture, which is believed to limit the rate of reaction of the reactants. However, it has been found that, following the production of by-product alcohol, the reaction mixture becomes monophasic, which is believed to be of benefit for the rate of reaction and the extent of glycerol conversion. As will be appreciated, the use of alcohol absorbent beds as in the case of some prior art processes is not considered to allow sufficient by-product alcohol to build-up to afford a monophasic reaction mixture. Furthermore, it has been surprisingly found that by incorporating an intermediate by-product alcohol separation step (ii) the conversion of glycerol to product is enhanced. Overall conversion has also been found to be especially favoured when the by-product alcohol separation step (ii) involves distillation of the reaction mixture, as discussed herein.

Meanwhile, it has also been found in preferred embodiments of the invention that selectivity for glycerol carbonate in the subsequent reaction in step (iii) which follows the alcohol separation step (ii) may be increased by ensuring that the subsequent reaction is performed with continuous by-product alcohol removal. It has been found that by incorporating continuous removal into the final stage of the reaction the overall selectivity for glycerol carbonate increases. Without being bound by any particular theory, it is believed that formation of glycerol dicarbonate occurs more readily in the subsequent reaction in step (iii) following the methanol separation step (ii), as illustrated in Scheme 3 below.

Scheme 3

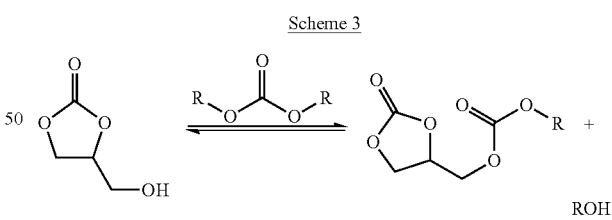

By employing continuous by-product alcohol removal in the final stage reaction in step (iii), it has been found that the equilibrium can be shifted towards the formation of the desired glycerol carbonate, as illustrated in Scheme 4 below.

Scheme 4

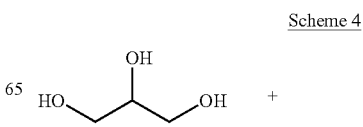

Scheme 2

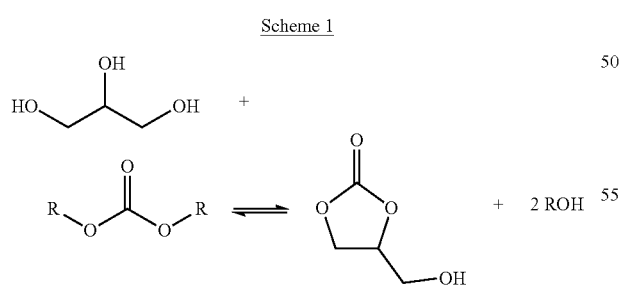

-continued

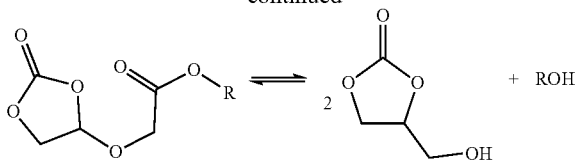 + ROH     2

The combination of the intermediate by-product alcohol separation step (ii) followed by continuous by-product alcohol removal in the subsequent reaction step (iii) may therefore maximise both conversion as well as selectivity for glycerol carbonate.

In accordance with the process of the present invention, in step (i) a glycerol reactant stream and a dialkyl carbonate reactant stream and/or cyclic alkylene carbonate reactant steam are contacted and partially reacted in a first reaction zone in the presence of a homogeneous transesterification catalyst.

The term "partially reacting" used herein is intended to refer to the incomplete reaction of glycerol and dialkyl carbonate/cyclic alkylene carbonate reactant streams such that residual reactants remain, in particular residual glycerol. Thus, partial or incomplete reaction of these streams corresponds to the situation where there is incomplete conversion of glycerol reactant, for example less than 90% conversion.

The term "reactant stream" used herein is intended to refer to a stream containing one of the reactants (i.e. either glycerol or dialkyl carbonate/cyclic alkylene carbonate) which is supplied for reaction as part of step (i).

The term "homogeneous transesterification catalyst" used herein is intended to refer to a catalyst which is in the same phase as the reactant streams. As such, the homogeneous transesterification catalyst will either by a liquid under the operating conditions of the process or at least partially soluble in a reactant stream and/or the reaction mixture under the operating conditions of the process. The term "catalyst" as used herein refers to a substance which increases the rate of a chemical reaction without itself being consumed by the reaction.

The term "glycerol carbonate product stream" used herein is intended to refer to a stream comprising glycerol carbonate product which is obtained from the reaction zone after step (iii) of the process has been conducted.

The terms "first reaction zone" and "second reaction zone" used herein are intended to refer to distinct and separate reaction regions within a system/apparatus where the reactions according to steps (i) and (iii) described herein are separately conducted. As will be appreciated, first and second reaction zones may be located within separate reactors, each reaction zone/reactor preferably being specifically configured for either reaction according to steps (i) or (iii), as applicable. Alternatively, first and second reaction zones may instead by located at different locations within the same reactor.

The dialkyl carbonate reactant stream comprises greater than 80 wt. % dialkyl carbonate. In preferred embodiments, the dialkyl carbonate reactant stream comprises greater than 90 wt. % dialkyl carbonate, more preferably greater than 95 wt. % dialkyl carbonate. In other preferred embodiments, the dialkyl carbonate reactant stream comprises less than 5 wt. % alcohol, preferably less than 2 wt. % alcohol, and more preferably less than 1 wt. % alcohol. The presence of alcohol, for example methanol, in the dialkyl carbonate reactant stream is preferably avoided, since this is likely to negatively impact the level of conversion of glycerol observed in step (i). In other preferred embodiments, the dialkyl carbonate reactant stream comprises less than 2 wt. % water, preferably less than 1 wt. % water.

As will be appreciated, the term "dialkyl" used in connection with the dialkyl carbonate reactant mentioned herein corresponds to two alkyl groups covalently bonded to separate oxygen atoms of the carbonate moiety. The two alkyl groups are preferably the same alkyl group, although they may be different, and can be substituted or preferably unsubstituted. Mixtures of dialkyl carbonates may be employed in the process of the present invention or a single dialkyl carbonate may be used.

In some embodiments, the two alkyl groups of the dialkyl carbonate are selected from $C_1$ to $C_6$ branched or preferably linear alkyl groups which may be substituted or unsubstituted. In preferred embodiments, the two alkyl groups of the dialkyl carbonate are selected from $C_1$ to $C_4$ branched or preferably linear alkyl groups. Examples of dialkyl carbonates for use with the present invention include: dimethyl carbonate, diethyl carbonate, dipropyl carbonate, dibutyl carbonate and dihexyl carbonate. Preferably, the dialkyl carbonate is dimethyl carbonate, diethyl carbonate or mixtures thereof. Most preferably, the dialkyl carbonate is dimethyl carbonate.

As will be appreciated, the nature of the dialkyl carbonate group employed in the process of the present invention determines the nature of the alcohol by-product which is produced as a result. For example, in a preferred embodiment where dimethyl carbonate is employed as the dialkyl carbonate reactant, methanol will be the by-product alcohol which is produced. Since the present invention relies on an interstage by-product alcohol separation from the reaction mixture, volatility in the by-product alcohol, particularly in comparison to the glycerol reactant, is desirable. This allows for a simple separation of by-product alcohol from the reaction mixture by feeding the reaction mixture to a flash column at reduced pressure.

The cyclic alkylene carbonate reactant stream which may be used alongside or in place of the dialkyl carbonate reactant stream comprises greater than 80 wt. % cyclic alkylene carbonate. In preferred embodiments, the cyclic alkylene carbonate reactant stream comprises greater than 90 wt. % cyclic alkylene carbonate, more preferably greater than 95 wt. % cyclic alkylene carbonate. In other preferred embodiments, the cyclic alkylene carbonate reactant stream comprises less than 5 wt. % alcohol, preferably less than 2 wt. % alcohol, and more preferably less than 1 wt. % alcohol. The presence of alcohol, for example methanol, in the cyclic alkylene carbonate reactant stream is preferably avoided, since this is likely to negatively impact the level of conversion of glycerol observed in step (i). In other preferred embodiments, the cyclic alkylene carbonate reactant stream comprises less than 2 wt. % water, preferably less than 1 wt. % water.

In preferred embodiments, the cyclic alkylene carbonate is of Formula I below:

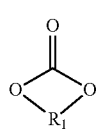

(I)

wherein:

$R_1$ is a divalent group, —$(CH_2)_n$—, wherein n is an integer of from 2 to 6, and which is unsubstituted or substituted by at least one $C_1$ to $C_6$ alkyl group, including a $C_1$ to $C_4$ alkyl group, or a $C_2$ to $C_3$ alkyl group.

In preferred embodiments, n is from 2 to 4, more preferably 2 or 3, most preferably 2. In other preferred embodiments, the divalent group, —$(CH_2)_n$—, is unsubstituted.

As will be appreciated, the nature of $R_1$ of the cyclic alkylene carbonate group employed in the process of the present invention determines the nature of the alcohol by-product which is produced as a result. For example, in a preferred embodiment where ethylene carbonate is employed as the cyclic alkylene carbonate reactant, ethylene glycol will be the by-product alcohol which is produced. Since the present invention relies on an interstage by-product alcohol separation from the reaction mixture, volatility in the by-product alcohol, particularly in comparison to the glycerol reactant, is desirable. This allows for a simple separation of by-product alcohol from the reaction mixture by feeding the reaction mixture to a flash column at reduced pressure.

Although the benefits of the invention may be realized using both a dialkyl carbonate and a cyclic alkylene carbonate reactant stream, the reaction of glycerol with a dialkyl carbonate is more favoured entropically in comparison to the reaction with a cyclic alkylene carbonate. For this reason, in preferred embodiments, the process of the present invention comprises the reaction of a dialkyl carbonate reactant stream in step (i).

The glycerol reactant stream may suitably comprise greater than 80 wt. % glycerol. In preferred embodiments, the glycerol reactant stream comprises greater than 90 wt. % glycerol, more preferably greater than 95 wt. % glycerol. In other preferred embodiments, the glycerol reactant stream comprises less than 5 wt. % water, more preferably less than 2 wt. % water, most preferably less than 1 wt. % water. The presence of water in the reaction is undesirable since it can lead to unwanted side reactions and lower the selectivity for glycerol carbonate. The presence of water may also have a negative impact on catalyst performance. The glycerol reactant stream, which is most susceptible to the presence of water, may therefore undergo a drying step, for instance using a distillation column and/or adsorbents such as molecular sieves, before it is used in the process of the present invention. Crude glycerol reactant may also undergo a colour/pigment removal step by passing over a bed of activated carbon absorbent in order to provide a higher purity starting material for use in the process of the invention.

The reactant streams may be combined before being fed to the first reaction zone for reaction in step (i) or they may be fed separately to the first reaction zone. Preferably, the reactant streams are combined before being fed to the first reaction zone for reaction in step (i). Turbulent flow and/or packing a mixing region with glass beads may be used to improve mixing of the dialkyl carbonate/cyclic alkylene carbonate and glycerol phases.

Any suitable molar ratio of dialkyl carbonate and/or cyclic alkylene carbonate to glycerol which favours the formation of glycerol carbonate can be used for reaction in step (i). However, at least stoichiometric levels of dialkyl carbonate and/or cyclic alkylene carbonate relative to glycerol are typically used. Preferably, for the reaction in step (i), the molar ratio of dialkyl carbonate and/or cyclic alkylene carbonate to glycerol is in the range of 1:1 to 3:1, preferably in the range of 1:1 to 2:1, more preferably in the range of 1.1:1 to 1.4:1, for example 1.2:1.

In some embodiments, the molar ratio of dialkyl carbonate and/or cyclic alkylene carbonate to glycerol is in the range of 0.7:1.0 to 1.0:1.0, for instance in the range of 0.75:1.0 to 0.95:1.0, or in the range of 0.8:1.0 to 0.9:1.0. In these embodiments, less dialkyl carbonate and/or cyclic alkylene carbonate is used such that the amount of dialkyl carbonate and/or cyclic alkylene carbonate that may be lost from the reaction mixture during the alcohol by-product separation step (discussed in more detail below) is reduced.

Glycerol conversion and selectivity for glycerol carbonate may be lessened by using close to or lower than stoichiometric amounts of dialkyl carbonate and/or cyclic alkylene carbonate. However, this may be balanced with lower costs associated with any dialkyl carbonate and/or cyclic alkylene carbonate recycle steps that may be integrated into the process (discussed in more detail below).

In preferred embodiments, the reactant streams are combined and reacted in the substantial absence of any solvents and/or diluents. For example, solvents and/or diluents are preferably present in the reaction mixture in an amount less than 500 ppm, more preferably less than 200 ppm.

The transesterification catalyst may be supplied to the first reaction zone for catalysing the reaction in step (i) directly or may be added to one or both of the reactant streams, or to a mixed reactant stream prior to being fed to the reaction zone. Preferably, the homogeneous transesterification catalyst is added to the glycerol reactant stream prior to being fed to the first reaction zone for reaction in step (i). Preferably, the homogeneous transesterification catalyst is present in the reaction mixture in an amount from 0.25 to 5 wt %, preferably from 0.5 to 1.5 wt %, for example 1 wt % based on the mass of glycerol supplied to the first reaction zone in step (i).

The temperatures and pressures at which the reaction in step (i) is undertaken may be any suitable temperatures and pressures which avoid decomposition of the reactants and minimise unwanted side reactions, such as polymerisation. Suitable reaction temperatures for step (i) are from 40 to 160° C., preferably from 60 to 140° C., more preferably 80 to 120° C. Suitable reaction pressures for step (i) are, for example, from 10 kPa absolute to 1,500 kPa absolute (0.1 to 15 bar absolute), preferably from 100 kPa absolute to 1,000 kPa absolute (1 to 10 bar absolute), and more preferably from 200 kPa absolute to 600 kPa absolute (2 to 6 bar absolute). Such reaction pressures may be autogenic pressures.

The reactant streams may be reacted in step (i) for any amount of time which is suitable for converting the majority of the glycerol present to product (i.e. converts 50 mol. % or more of the glycerol present) but does not completely consume the glycerol reactant. For example, reaction in step (i) may be conducted for from 10 minutes to 12 hours, preferably from 20 minutes to 3 hours, more preferably from 30 minutes to 1 hour, for example 45 mins. In preferred embodiments, step (i) achieves from 50 to 90 mol. % glycerol conversion, preferably from 70 to 90 mol. %, most preferably from 80 to 90 mol. % glycerol conversion. As the skilled person will appreciate, optimising the mixing of the reactants, e.g. by employing mechanical mixing of reactants, can increase reaction rate.

In step (ii) of the process of the invention, at least a portion of the by-product alcohol formed in step (i) is separated from the reaction mixture. As will be appreciated by the skilled person, the term "separate" is intended to refer to the physical extraction of alcohol by-product from the reaction mixture. In particular, separation in the context of the present invention is such that an alcohol-containing by-product stream is obtained as a result. As will be appreciated by the skilled person, the use of adsorbents that may come into contact with the reaction mixture and immobilise alcohol by-product is not considered to separate alcohol so as to obtain an alcohol-containing by-product stream in accordance with the present invention.

Separation of alcohol as part of step (ii) may be achieved by any means of which the skilled person is aware, provided that an alcohol-containing by-product stream is obtained directly therefrom and can be further processed. Preferably, separation of alcohol in step (ii) is by means of a flash vessel operating under reduced pressure in order to separate the volatile components of the reaction mixture, including alcohol, or a distillation column. More preferably, the alcohol separation step (ii) is performed using a distillation column. The distillation may be a conventional distillation column with a number of stages (e.g. ideal stages) commensurate with the separation desired, for example between about 5 and about 50 ideal separation stages.

In some embodiments, the alcohol separation step (ii) removes greater than 50 wt. % of the alcohol by-product. Preferably, greater than 75 wt. % of the alcohol by-product is separated from the reaction mixture in step (ii), even more preferably greater than 90 wt. %, most preferably greater than 95 wt. % of the alcohol by-product is separated from the reaction mixture in step (ii).

Where the alcohol separation step is achieved using a distillation column, a suitable range of pressure over which distillation may be performed is from 50 mbar absolute to 1 bar absolute. In preferred embodiments, the pressure range over which distillation is performed is from 100 to 700 mbar absolute, preferably from 200 to 500 mbar absolute, more preferably from 300 to 400 mbar absolute. As will be understood by the skilled person, as pressure is increased in the distillation column, higher temperatures are typically required for effective distillation. For example, in the present case, where a relatively high pressure of 1 bar is used for distillation, temperatures of over 80° C. may be required. In contrast, at pressures lower than 100 mbar absolute, a distillation temperature as low as 30° C. may be suitable.

Where the alcohol separation step is achieved using a distillation column, a suitable temperature range over which distillation may be performed is 35 to 90° C. In the presence of homogeneous catalyst and in the absence of significant amounts of alcohol and dialkyl carbonate/cyclic alkylene carbonate, as is the case in stages of the distillation, unwanted polymerisation of glycerol carbonate can become more prevalent. So as to avoid significant amounts of polymerisation and other side reactions which become more prevalent at higher temperatures, distillation temperatures should not exceed 90° C. In preferred embodiments, the temperature range over which distillation is performed as part of the alcohol separation is from 40° C. to 80° C., more preferably from 50° C. to 70° C., for example a temperature of 60° C.

In addition, it has also been found that increasing the distillation pressure as far as is practicable for achieving effective separation at the particular distillation temperature employed can also have a beneficial effect on glycerol conversion and yield of glycerol carbonate, prior to further reaction in step (iii). As will be appreciated, separation in the distillation column typically requires elevated temperatures. Thus, it can be expected that further reaction of the reactants can take place during the separation process, which can contribute further to conversion of glycerol prior to further reaction in step (iii). By maximising the distillation pressure for the distillation temperature that is employed, additional glycerol conversion may be observed prior to reaction in step (iii). In an exemplary embodiment, where a distillation temperature of from 35° C. to 45° C., for example 40° C., is used the distillation column may advantageously be operated at pressure of 100 to 150 mbar absolute, for example 120 mbar absolute.

As a result of the similar boiling properties of the dialkyl carbonate or cyclic alkylene carbonate reactants and the respective alcohol by-products produced therefrom, these components may form part of an azeotropic mixture with by-product alcohol during the alcohol separation step (ii). For instance, it is known that methanol forms an azeotrope with dimethyl carbonate as a result of their similar boiling properties. Consequently, alcohol by-product separation step (ii) is typically accompanied by removal of an amount of unreacted dialkyl carbonate or cyclic alkylene carbonate from the reaction mixture, which is normally present in excess compared with the glycerol reactant. However, it has also been found that the composition of the azeotrope is sensitive to pressure. Where the alcohol separation step (ii) is achieved using a distillation column, it has been found that modifying the pressure can reduce the dialkyl carbonate/cyclic alkylene carbonate content of the resulting azeotrope. For example, it has been found that increasing the pressure in the distillation column decreases the proportion of dimethyl carbonate in a methanol/dimethyl carbonate azeotropic mixture, meaning that more dimethyl carbonate reactant is retained in the reaction mixture for subsequent reaction after methanol separation in step (ii).

By mitigating dialkyl carbonate/cyclic alkylene carbonate loss during the alcohol separation step (ii), there is less reliance on an additional dialkyl carbonate/cyclic alkylene carbonate reactant supply stream for replenishing dialkyl carbonate/cyclic alkylene carbonate levels specifically for the second stage reaction in step (iii). In some embodiments, careful selection of the conditions for the alcohol separation step (ii), coupled with the use of a high proportion of dialkyl carbonate/cyclic alkylene carbonate for the first stage reaction in step (i), mean that it may not be necessary to replenish dialkyl carbonate/cyclic alkylene carbonate levels after the alcohol separation step (ii) in order to achieve adequate glycerol conversion and/or overall yield of glycerol carbonate.

In preferred embodiments of the invention, an additional dialkyl carbonate/cyclic alkylene carbonate reactant supply stream is used to replenish levels of dialkyl carbonate/cyclic alkylene carbonate in the reaction mixture specifically for reaction in step (iii) of the process. For instance, additional dialkyl carbonate/cyclic alkylene carbonate reactant may be added to replace dialkyl carbonate/cyclic alkylene carbonate lost as a result of the alcohol separation step (ii). Alternatively or additionally, additional dialkyl carbonate/cyclic alkylene carbonate reactant may be added to increase the ratio of dialkyl carbonate/cyclic alkylene carbonate to unreacted glycerol for reaction in step (iii) compared with the ratio of dialkyl carbonate/cyclic alkylene carbonate to glycerol used for reaction in step (i). Levels of dialkyl carbonate/cyclic alkylene carbonate are preferably maintained at least at stoichiometric levels relative to glycerol throughout the process of the present invention.

In some embodiments, the additional dialkyl carbonate/cyclic alkylene carbonate reactant supply stream used to replenish levels of dialkyl carbonate/cyclic alkylene carbonate in the reaction mixture specifically for reaction in step (iii) of the process may correspond to a dialkyl carbonate/ cyclic alkylene carbonate recycle stream obtained from an alcohol-dialkyl carbonate/cyclic alkylene carbonate separation step. For example, a separation step may be conducted on an azeotropic mixture of alcohol and dialkyl carbonate/cyclic alkylene carbonate obtained from the alcohol separation step (ii). Alternatively or additionally, a separation step may be conducted on a mixture comprising alcohol and dialkyl carbonate/cyclic alkylene carbonate separated from the glycerol carbonate stream obtained in step (iv).

Addition of further dialkyl carbonate/cyclic alkylene carbonate reactant may be via a separate stream which is mixed with the remaining reaction mixture obtained following the alcohol separation step (ii). Alternatively, additional dialkyl carbonate/cyclic alkylene carbonate may be supplied via a stream directly feeding the second reaction zone used for reaction in step (iii), at which point the additional dialkyl carbonate/cyclic alkylene carbonate comes into contact with the remaining reaction mixture from alcohol separation step (ii).

As for reaction in step (i), any suitable molar ratio of dialkyl carbonate/cyclic alkylene carbonate to glycerol may be used which favours the formation of glycerol carbonate can be used for reaction in step (iii). However, at least stoichiometric levels of dialkyl carbonate/cyclic alkylene carbonate relative to glycerol are typically used.

As will be appreciated, as two separate reaction zones are used for reaction in steps (i) and (iii), a different ratio of dialkyl carbonate/cyclic alkylene carbonate to glycerol may be used for each of these reaction steps. In preferred embodiments, the ratio of dialkyl carbonate and/or cyclic alkylene carbonate to glycerol employed in the first and second reaction zones is different. Preferably, for the reaction in step (iii) the molar ratio of dialkyl carbonate and/or cyclic alkylene carbonate to glycerol is in the range of 1.5:1 to 4:1, preferably 1.75:1 to 3.5:1, more preferably 2.0:1 to 3.0:1, for example 2.5:1.

It has been found to be beneficial if a higher ratio of dialkyl carbonate and/or cyclic alkylene carbonate to unreacted glycerol is used for reaction step (iii) compared with the ratio of dialkyl carbonate and/or cyclic alkylene carbonate to glycerol employed for reaction in step (i). In particular, use of a relatively low ratio of dialkyl carbonate and/or cyclic alkylene carbonate to glycerol in step (i), whilst typically having at least stoichiometric amounts of dialkyl carbonate, and a relatively higher ratio of dialkyl carbonate and/or cyclic alkylene carbonate to glycerol in step (iii) has been found to enhance even further the overall glycerol conversion that is observed and the yield of glycerol carbonate product. In a particularly preferred embodiment of the invention, the dialkyl carbonate and/or cyclic alkylene carbonate to glycerol molar ratio employed in step (i) is 1.1:1 to 1.4:1 and the dialkyl carbonate and/or cyclic alkylene carbonate to glycerol molar ratio employed in step (iii) is 2.0:1 to 3.0:1.

In step (iii) of the process of the present invention, at least a portion of the remaining reactants following alcohol separation step (ii) are reacted in the presence of the homogeneous transesterification catalyst in a reaction zone. Preferably, substantially all of the remaining reactants present following separation step (ii) are reacted in the presence of the homogeneous transesterification catalyst in a reaction zone. The transesterification catalyst will typically be stable at the process conditions employed and have a volatility such that there are minimal catalyst losses as a result of the alcohol removal step. Therefore, it is not expected to be necessary to top-up the content of homogeneous transesterification catalyst in the reaction mixture before undertaking reaction in step (iii), although this is not precluded.

As will be appreciated, the first reaction zone employed for step (i) may be operated under the same or different conditions of temperature and pressure to those of the second reaction zone employed for step (iii) of the process. As with step (i) the temperatures and pressures at which the reaction in step (iii) is undertaken may be any suitable temperatures and pressures which avoid decomposition of the reactants and minimise unwanted side reactions, such as polymerisation.

In some embodiments, the conditions of temperature and pressure in the first and second reaction zones are different. For instance, as a result of the alcohol separation step (ii), there will be a pressure drop between the first reaction zone and the second reaction zone which may mean that the second reaction zone is operated at lower pressure than the first reaction zone. Suitable reaction temperatures for step (iii) are from 20 to 160° C., preferably from 40 to 140° C., more preferably 80 to 120° C. Suitable reaction pressures for step (iii) are from 5 kPa absolute to 150 kPa absolute (0.05 to 1.5 bar absolute), more preferably from 10 kPa absolute to 100 kPa absolute (0.1 to 1 bar absolute), and most preferably 15 kPa absolute to 50 kPa absolute (0.15 to 0.5 bar absolute).

The first and second reaction zones may be located within any liquid-phase reactors including but not limited to plug flow, continuously stirred tank, or loop reactors, or combinations thereof. Reactive separations, such as reactive distillation, can also be employed in accordance with the present invention and are particularly useful in a continuous process where production and removal of products/by-products occurs simultaneously. The use of reactive distillation columns is advantageous insofar as they are multifunctional reactors, where reactive and separation tasks may be combined into a single unit, thereby reducing capital costs. The skilled person is aware of the ways in which a distillation column arrangement can be modified so as to take full advantage of rectification and stripping as liquid flows downwards and vapour flows upwards within the column for a given reaction. Typically, the reactants are fed to the column at a location where the feed enthalpy and composition minimizes energy for a given separation requirement.

In some embodiments, the first and second reaction zones are located within first and second reactors respectively. First and second reactors may both, for example, be plug flow reactors, which allows for continuous operation of the process. Plug flow reactors are also advantageous for eliminating back filling of the reactors, which can lead to unwanted further reaction of products (e.g. further reaction of glycerol carbonate to form glycerol dicarbonate).

In preferred embodiments, the second reactor is configured for continuous by-product alcohol removal. Any form of reactor of which the person of skill in the art is familiar and which is capable of achieving that separation may be used. For instance, a reactive distillation column may suitably be used for that purpose. Any suitable reactive distillation column may be used provided it is configured for continuous alcohol removal and has a number of stages (e.g. ideal stages) commensurate with the separation desired, for example between about 5 and about 50 ideal separation stages. The internal components of the distillation column may include, for example, sieve plates, unstructured and structured packing, bubble cap and mixtures thereof. For example, in the case of a reactive distillation column configured for by-product alcohol removal, alcohol vapour may be collected from a rectification section, without being returned to the reaction zone. Meanwhile, vaporized dialkyl carbonate and/or cyclic alkylene carbonate reactant may be re-condensed and returned to the reaction zone, for example a tray thereof, as liquid and product glycerol carbonate can be continuously withdrawn from the bottom of the stripping zone.

As discussed hereinbefore, it has been found that continuous by-product alcohol removal during reaction in step (iii) of the process is particularly beneficial for the selectivity of the reaction to glycerol carbonate. In particular, continuous alcohol removal during step (iii) is believed to shift the dynamic reaction equilibrium towards formation of glycerol carbonate. What is more, it has also surprisingly been found that continuous alcohol removal also actively reduces the levels of glycerol dicarbonate by-product. For instance, even where the reactant/product mixture which is further reacted in step (iii) initially comprises glycerol dicarbonate (formed reversibly from the further reaction of glycerol carbonate product with a carbonate reactant), it is possible that further reaction in step (iii) together with continuous by-product alcohol removal may convert glycerol dicarbonate into the desired glycerol carbonate product. Thus, in preferred embodiments, the process further comprises continuous removal of alcohol by-product formed during step (iii) of the process.

In some embodiments, first and second reaction zones are located within a single reactor. Again, it is also preferred that the single reactor is configured such that continuous by-product alcohol removal is possible during reaction in step (iii) of the process.

According to step (iv) of the process, a glycerol carbonate product stream is obtained following the further reaction in step (iii). The glycerol carbonate product stream may correspond to the product stream which is withdrawn directly from the reactor following reaction in step (iii). The glycerol carbonate product stream may be further processed in order to remove a) any unreacted glycerol and/or dialkyl carbonate/cyclic alkylene carbonate; b) any alcohol by-product; and c) homogeneous transesterification catalyst.

In preferred embodiments, the process of the invention further comprises a step of separating the homogeneous transesterification catalyst from the glycerol carbonate product stream which is obtained in step (iv). As the skilled person is aware, the nature of this separation is dependent on the nature of the homogeneous transesterification catalyst which is employed. Where the transesterification catalyst is ionic in nature (e.g. a salt), the separation may be achieved using anionic or cationic exchange processes. In preferred embodiments, an ionic transesterification catalyst is removed by contacting the glycerol carbonate product stream with a cation exchange resin absorbent. Where the transesterification catalyst is a non-ionic, basic compound (e.g. an amine compound such as TMDH-piperidine discussed below) the use of a protic cation exchange resin absorbent has also been found to be suitable for separating the catalyst from the glycerol carbonate product stream.

Examples of suitable cation exchange resins include Purolite C107E—macroporous weak acid cation exchange resin based upon polyacrylic acid; Amberlite IR120 ($H^+$ form)—strongly acidic cation exchange resin based on sulfonic acid groups tethered to crosslinked polystyrene beads; and Amberlyst 15 ($H^+$ form)—macroreticular (large pore size) sulfonic acid cation exchange resin. In preferred embodiments, the glycerol carbonate product stream is passed through a column packed with the cation exchange resin absorbent.

Where a cation exchange resin absorbent is used for separating the homogeneous transesterification catalyst from the glycerol carbonate product stream, the resin may be regenerated by washing with water, drying and contacting with acid (e.g. HCl).

In some embodiments, the process further comprises a step of recovering unreacted dialkyl carbonate/cyclic alkylene carbonate and/or alcohol by-product from the glycerol carbonate product stream. Separation of dialkyl carbonate/cyclic alkylene carbonate and/or alcohol by-product may be achieved by means of a flash vessel operating under reduced pressure in order to separate the volatile components of the glycerol carbonate product stream, including alcohol, or a distillation column. However, where a reactive distillation column is employed in step (iii) of the process, all alcohol and dialkyl carbonate and/or cyclic alkylene carbonate reactant is expected to be separated from the glycerol carbonate product stream which is obtained from the reaction.

Where an azeotropic mixture of dialkyl carbonate and the alcohol by-product derived therefrom or cyclic alkylene carbonate and the alcohol by-product derived therefrom is obtained from the process of the present invention, in particular where the mixture comprises methanol and/or ethanol, this mixture may be used to supply a downstream biodiesel production plant and therefore may represent a further revenue stream for the process. Alternatively, the azeotropic mixture may be separated in order to obtain, for instance, a dialkyl carbonate/cyclic alkylene carbonate recycle stream and a commercially valuable alcohol by-product stream.

Thus, where a stream comprising an azeotropic mixture of unreacted dialkyl carbonate reactant/cyclic alkylene carbonate and by-product alcohol is obtained as part of the process, in some embodiments the process further comprises a step of separating the unreacted dialkyl carbonate/cyclic alkylene carbonate and by-product alcohol in the azeotropic mixture. Preferably, the separation step is used to produce a dialkyl carbonate recycle steam which may be used as a source of dialkyl carbonate for reaction at any suitable stage in the process of the invention described hereinbefore. Separation of alcohol and dialkyl carbonate/cyclic alkylene carbonate may be achieved by any process of which the skilled person is familiar and which is suitable for obtaining a dialkyl carbonate/cyclic alkylene carbonate recycle stream. Examples of suitable separation processes include pressure swing distillation and extractive distillation, for instance, using methyl isobutyl ketone (MIBK) entrainer solvent for the separation of methanol/dimethyl carbonate.

The homogeneous transesterification catalyst used in the present invention is not particularly limited provided that it is in a liquid phase (i.e. dissolved in the reaction mixture or a reactant stream, or in a liquid state itself) under the operating conditions of the process. The homogeneous transesterification catalyst in accordance with the present invention catalyses the formation of glycerol carbonate from glycerol and dialkyl carbonate/cyclic alkylene carbonate reactants without itself being consumed by the reaction (i.e. not acting as a reactant without subsequently being regenerated). Advantageously, the use of a homogeneous transesterification catalyst means that no special start-up conditions or induction period is necessary for commencing the process of the present invention, which is often required in the case of heterogeneous transesterification catalysts.

In some embodiments, the homogeneous transesterification catalyst is in a liquid state under the operating conditions of the process. In other embodiments, the transesterification catalyst is soluble in a reactant stream and/or the reaction mixture under the operating conditions of the process. The transesterification catalyst may be added to the reaction in the form of a solution, wherein the transesterification catalyst is dissolved in a suitable, preferably non-aqueous, solvent and preferably where the solvent has been pre-dried to remove water. A suitable solvent may for instance be an alcohol which is the by-product of the dialkyl carbonate/cyclic alkylene carbonate reactant employed in the reaction. For example, where dimethyl carbonate reactant is used, the transesterification catalyst may be present in a concentrated methanolic solution. However, it is preferred that the homogeneous transesterification catalyst is provided without requiring the use of a solvent.

Suitable homogeneous transesterification catalysts include basic catalysts selected from alkali metal carbonate, alkali metal bicarbonate, alkali metal hydroxide, alkali metal oxide, alkali metal alkoxide, alkali metal aluminate, alkali metal silicate, alkaline earth metal carbonate, alkaline earth metal bicarbonate, alkaline earth metal hydroxide, alkaline earth metal oxide, alkaline earth metal alkoxide, alkaline earth metal aluminate, alkaline earth metal silicate and combinations thereof. In preferred embodiments, the homogeneous transesterification catalyst is an alkali metal alkoxide. Reference to "alkoxide" herein includes $C_1$ to $C_6$ straight chain or branched alkoxides, for example $C_1$ to $C_2$ alkoxides. Specific examples of suitable homogeneous transesterification catalysts include NaOMe, $Na_2CO_3$, $NaHCO_3$, $K_2CO_3$, $KHCO_3$, and $Na_2SiO_3$, preferably NaOMe.

The below reaction Scheme 5 illustrates a possible mechanism for the base-catalysed transesterification of dimethyl carbonate.

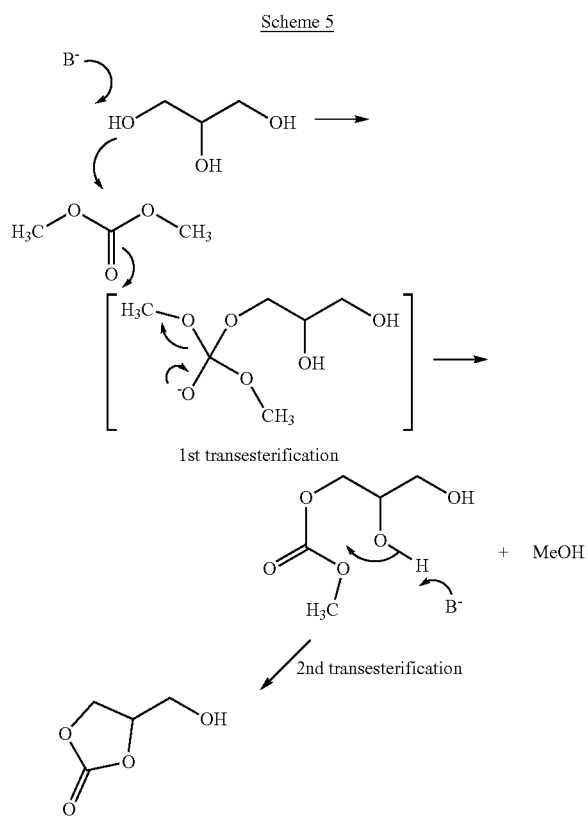

Scheme 5

A particularly preferred transesterification catalyst for use in the present invention is NaOMe, which is soluble in glycerol. NaOMe has been found to be particularly advantageous in the process of the present invention. Specifically, use of NaOMe in the process of the present invention has been found to afford a high level of conversion to glycerol carbonate within short time frames and at relatively low reaction temperatures. For instance, 90% conversion to glycerol carbonate in step (i) of the process described herein is observed within as little as 20 minutes of reaction time, for a dimethyl carbonate:glycerol molar ratio of 2:1, and at a reaction temperature of only 80° C.

In another aspect, the present invention provides a process for preparing glycerol carbonate comprising the steps of:

(i) reacting a glycerol reactant stream with: a) a dialkyl carbonate reactant stream; and/or b) a cyclic alkylene carbonate reactant stream, in a reactor in the presence of a homogeneous transesterification catalyst; and (ii) obtaining a glycerol carbonate product stream;

wherein the homogeneous transesterification catalyst is sodium methoxide. Preferably, the reaction is conducted at a temperature of less than 110° C., more preferably from 50° C. to 100° C., even more preferably from 70° C. to 90° C., most preferably from 75° C. to 85° C., for example 80° C. As will be appreciated, any preferred embodiments relating to the nature and processing of reactant and product streams described hereinbefore apply equally to this aspect of the invention.

Other suitable transesterification catalysts include ionic liquids. The term "ionic liquid" as used herein refers to a liquid that is capable of being produced by melting a salt, and when so produced consists solely of ions. An ionic liquid may be formed from a homogeneous substance comprising one species of cation and one species of anion, or it can be composed of more than one species of cation and/or more than one species of anion. Thus, an ionic liquid may be composed of more than one species of cation and one species of anion. An ionic liquid may further be composed of one species of cation, and one or more species of anion. Still further, an ionic liquid may be composed of more than one species of cation and more than one species of anion.

The term "ionic liquid" includes compounds having both high melting points and compounds having low melting points, e.g. at or below room temperature. Thus, many ionic liquids have melting points below 200° C., particularly below 100° C., around room temperature (15 to 30° C.), or even below 0° C. Ionic liquids having melting points below around 30° C. are commonly referred to as "room temperature ionic liquids" and are often derived from organic salts having nitrogen-containing heterocyclic cations. In room temperature ionic liquids, the structures of the cation and anion prevent the formation of an ordered crystalline structure and therefore the salt is liquid at room temperature.

Ionic liquids are most widely known as solvents. Many ionic liquids have been shown to have negligible vapour pressure, temperature stability, low flammability and recyclability. Due to the vast number of anion/cation combinations that are available it is possible to fine-tune the physical properties of the ionic liquid (e.g. melting point, density, viscosity, and miscibility with water or organic solvents) to suit the requirements of a particular application.

Ionic liquid homogeneous transesterification catalysts for use in the present invention have the formula:

[Cat⁺][X⁻]

wherein: [Cat⁺] represents one or more cationic species; and
[X⁻] represents one or more basic anionic species.

In accordance with the present invention, [Cat⁺] may comprise a cationic species selected from: ammonium, benzimidazolium, benzofuranium, benzothiophenium, benzotriazolium, diazabicyclodecenium, diazabicyclononenium, 1,4-diazabicyclo[2.2.2]octanium, diazabicyclo-undecenium, dithiazolium, furanium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, triazinium, triazolium, and iso-triazolium.

In one preferred embodiment of the invention, [Cat⁺] comprises an acyclic cation selected from:

[N(R$^a$)(R$^b$)(R$^c$)(R$^d$)]⁺, [P(R$^a$)(R$^b$)(R$^c$)(R$^d$)]⁺, and [S(R$^a$)(R$^b$)(R$^c$)]⁺, wherein: R$^a$, R$^b$, R$^c$, and R$^d$ are each independently selected from a $C_1$ to $C_{30}$, straight chain or branched alkyl group, a $C_3$ to $C_8$ cycloalkyl group, or a $C_6$ to $C_{10}$ aryl group; and wherein said alkyl, cycloalkyl or aryl groups are unsubstituted or may be substituted by one to three groups selected from: $C_1$ to $C_6$ alkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —NO$_2$, —C(S)R$^x$, —CS$_2$R$^x$, —SC(S)R$^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S ($C_1$ to $C_6$alkyl), —NR$^y$R$^z$, or a heterocyclic group, wherein R$^x$, R$^y$ and R$^z$ are independently selected from hydrogen or $C_1$ to $C_6$ alkyl.

More preferably, [Cat⁺] comprises a cation selected from:

[N(R$^a$)(R$^b$)(R$^c$)(R$^d$)]⁺, [P(R$^a$)(R$^b$)(R$^c$)(R$^d$)]+, and [S(R$^a$)(R$^b$)(R$^c$)]⁺, wherein: R$^a$, R$^b$, R$^c$, and R$^d$ are each independently selected from a $C_1$ to $C_{15}$ straight chain or branched alkyl group, a $C_3$ to $C_6$ cycloalkyl group, or a $C_6$ aryl group; and wherein said alkyl, cycloalkyl or aryl groups are unsubstituted or may be substituted by one to three groups selected from: $C_1$ to $C_6$ alkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —NO$_2$, —C(S)R$^x$, —CS$_2$R$^x$, —SC(S)R$^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S ($C_1$ to $C_6$ alkyl), —NR$^y$R$^z$, or a heterocyclic group, wherein R$^x$, R$^y$ and R$^z$ are independently selected from hydrogen or $C_1$ to $C_6$ alkyl.

Further examples include wherein R$^a$, R$^b$, R$^c$ and R$^d$ are independently selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl. More preferably two or more, and most preferably three or more, of R$^a$, R$^b$, R$^c$ and R$^d$ are selected from methyl, ethyl, propyl and butyl.

Still more preferably, [Cat⁺] comprises a cation selected from:

[N(R$^a$)(R$^b$)(R$^c$)(R$^d$)]⁺, wherein: R$^a$, R$^b$, R$^c$, and R$^d$ are as defined above.

In a preferred further embodiment, [Cat⁺] preferably comprises a cation selected from:

[P(R$^a$)(R$^b$)(R$^c$)(R$^d$)]⁺, wherein: R$^a$, R$^b$, R$^c$, and R$^d$ are as defined above.

Specific examples of preferred ammonium and phosphonium cations suitable for use according to the present invention include:

$\overset{+}{\text{NMe}_4}$   $\overset{+}{\text{PMe}_4}$   $\overset{+}{\text{NBu}_4}$   $\overset{+}{\text{PBu}_4}$ ([N$_{1,1,1,1}$]),  ([P$_{1,1,1,1}$]),  ([N$_{4,4,4,4}$]),  ([P$_{4,4,4,4}$]), $\overset{+}{\text{NHBu}_3}$   $\overset{+}{\text{Et}_3\text{NMe}}$   $\overset{+}{\text{NMeBu}_3}$   $\overset{+}{(\text{C}_8\text{H}_{17})_3\text{NMe}}$ ([NH$_{4,4,4}$]),  ([N$_{2,2,2,1}$]),  ([N$_{4,4,4,1}$]),  ([N$_{8,8,8,1}$]) , $\overset{+}{\text{NBuMe}_3}$   $\overset{+}{(\text{C}_8\text{H}_{17})\text{NMe}_3}$ ([N$_{4,1,1,1}$]),  ([N$_{8,1,1,1}$]) , Specific examples of more preferred ammonium cations suitable for use according to the present invention include:

$\overset{+}{\text{NMe}_4}$,   $\overset{+}{\text{Et}_3\text{NMe}}$,   and   $\overset{+}{\text{NMeBu}_3}$ ([N$_{1,1,1,1}$])   ([N$_{2,2,2,1}$])   ([N$_{4,4,4,1}$]).

A particular preferred example of an ammonium cation suitable for use according to the present invention is:

$\overset{+}{\text{Et}_3\text{NMe}}$, ([N$_{2,2,2,1}$])

In a further preferred embodiment, [Cat⁺] comprises a cation comprising an electron-rich sulfur or selenium moiety. Examples include cations as defined above comprising pendant thiol, thioether, or disulfide substituents.

In another embodiment of the invention, [Cat⁺] comprises an aromatic heterocyclic cationic species selected from: benzimidazolium, benzofuranium, benzothiophenium, benzotriazolium, diazabicyclodecenium, diazabicyclononenium, diazabicyclo-undecenium, dithiazolium, imidazolium, indazolium, indolinium, indolium, oxazinium, oxazolium, iso-oxazolium, oxathiazolium, phthalazinium, pyrazinium, pyrazolium, pyridazinium, pyridinium, pyrimidinium, quinazolinium, quinolinium, iso-quinolinium, quinoxalinium, tetrazolium, thiadiazolium, iso-thiadiazolium, thiazinium, thiazolium, iso-thiazolium, triazinium, triazolium, and iso-triazolium.

More preferably, [Cat⁺] has the formula:

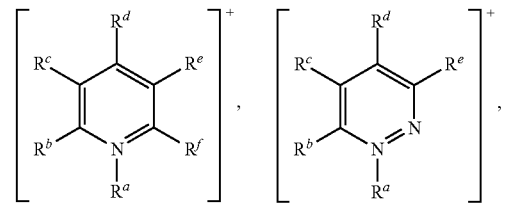

-continued

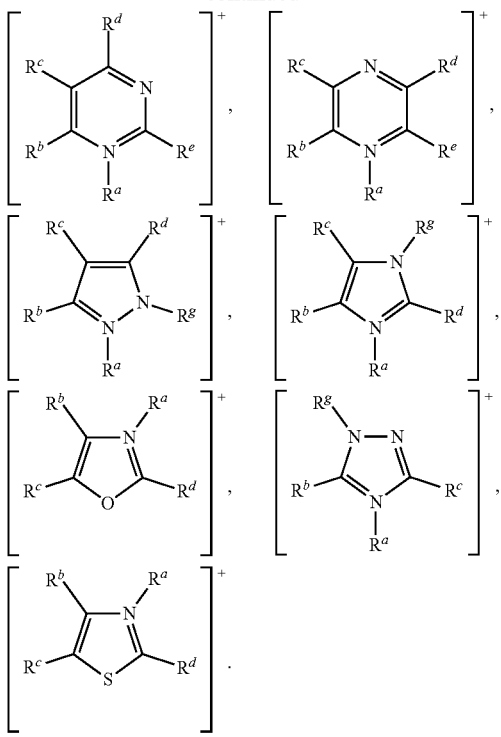

wherein: $R^a$, $R^b$, $R^c$, $R^d$, $R^e$, $R^f$ and $R^g$ are each independently selected from hydrogen, a $C_1$ to $C_{30}$, straight chain or branched alkyl group, a $C_3$ to $C_8$ cycloalkyl group, or a $C_6$ to $C_{10}$ aryl group, or any two of $R^b$, $R^c$, $R^d$, $R^e$ and $R^f$ attached to adjacent carbon atoms form a methylene chain —$(CH_2)_q$— wherein q is from 3 to 6; and wherein said alkyl, cycloalkyl or aryl groups or said methylene chain are unsubstituted or may be substituted by one to three groups selected from: $C_3$ to $C_8$ cycloalkyl, $C_6$ to $C_{10}$ aryl, $C_7$ to $C_{10}$ alkaryl, $C_7$ to $C_{10}$ aralkyl, —CN, —$NO_2$, —$C(S)R^x$, —$CS_2R^x$, —SC(S)$R^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S($C_1$ to $C_6$ alkyl), —SC(S)$NR^yR^z$, —$NR^yR^z$, or a heterocyclic group, wherein $R^x$, $R^y$ and $R^z$ are independently selected from hydrogen or $C_1$ to $C_6$ alkyl.

$R^a$ is preferably selected from $C_1$ to $C_{30}$, linear or branched, alkyl, more preferably $C_2$ to $C_{20}$ linear or branched alkyl, still more preferably, $C_2$ to $C_{10}$ linear or branched alkyl, and most preferably $C_4$ to $C_8$ linear or branched alkyl. Further examples include wherein $R^a$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the cations comprising an $R^g$ group, $R^g$ is preferably selected from $C_1$ to $C_{10}$ linear or branched alkyl, more preferably, $C_1$ to $C_5$ linear or branched alkyl, and most preferably $R^g$ is a methyl group.

In the cations comprising both an $R^a$ and an $R^g$ group, $R^a$ and $R^g$ are each preferably independently selected from $C_1$ to $C_{30}$, linear or branched, alkyl, and one of $R^a$ and $R^g$ may also be hydrogen. More preferably, one of $R^a$ and $R^g$ may be selected from $C_2$ to $C_{20}$ linear or branched alkyl, still more preferably, $C_2$ to $C_{10}$ linear or branched alkyl, and most preferably $C_4$ to $C_8$ linear or branched alkyl, and the other one of $R^a$ and $R^g$ may be selected from $C_1$ to $C_{10}$ linear or branched alkyl, more preferably, $C_1$ to $C_5$ linear or branched alkyl, and most preferably a methyl group. In a further preferred embodiment, $R^a$ and $R^g$ may each be independently selected, where present, from $C_1$ to $C_{30}$ linear or branched alkyl and $C_1$ to $C_{15}$ alkoxyalkyl.

In further preferred embodiments, $R^b$, $R^c$, $R^d$, $R^e$, and $R^f$ are independently selected from hydrogen and $C_1$ to $C_5$ linear or branched alkyl, and more preferably $R^b$, $R^c$, $R^d$, $R^e$, and $R^f$ are hydrogen.

In this embodiment of the invention, [Cat$^+$] preferably comprises a cation selected from:

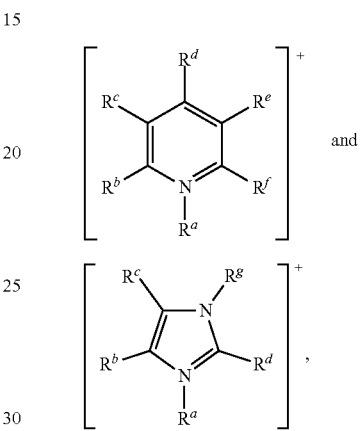

and wherein: $R^a$, $R^b$, $R^c$, $R^d$, $R^e$, $R^f$, and $R^g$ are as defined above.

More preferably, [Cat$^+$] comprises a cation selected from:

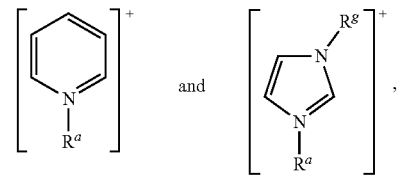

and wherein: $R^a$ and $R^g$ are as defined above.

Also in accordance with this embodiment of the invention, [Cat$^+$] may preferably comprise a cation selected from:

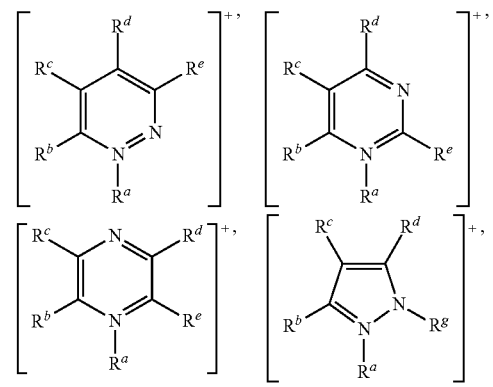

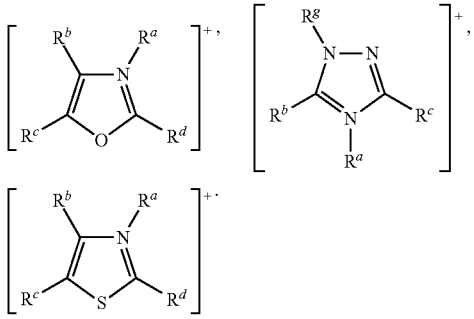

wherein: $R^a$, $R^b$, $R^c$, $R^d$, $R^e$, $R^f$ and $R^g$ are as defined above.

Specific examples of preferred nitrogen-containing aromatic heterocyclic cations that may be used according to the present invention include:

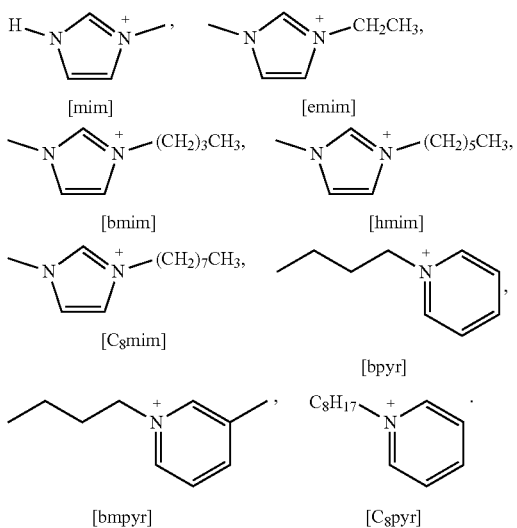

In another preferred embodiment of the invention, [Cat$^+$] comprises a saturated heterocyclic cation selected from cyclic ammonium, 1,4-diazabicyclo[2.2.2]octanium, morpholinium, cyclic phosphonium, piperazinium, piperidinium, quinuclidinium, and cyclic sulfonium.

More preferably, [Cat$^+$] comprises a saturated heterocyclic cation having the formula:

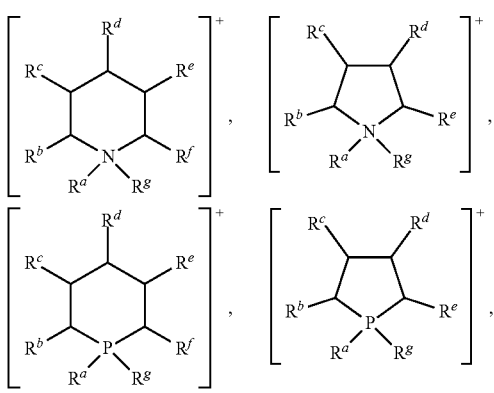

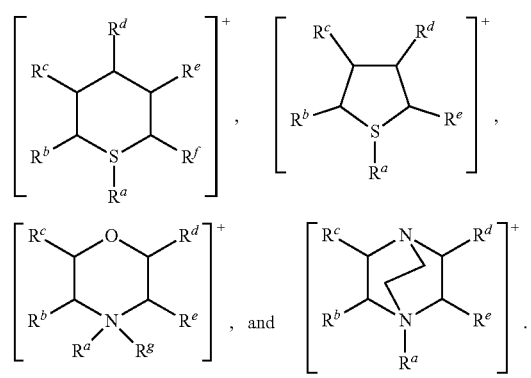

wherein: $R^a$, $R^b$, $R^c$, $R^d$, $R^e$, $R^f$, and $R^g$ are as defined above.

Still more preferably, [Cat$^+$] comprises a saturated heterocyclic cation having the formula:

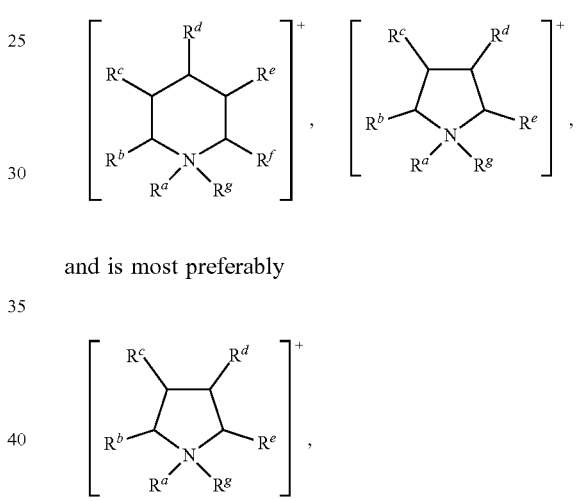

and is most preferably

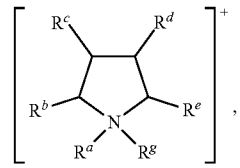

wherein: $R^a$, $R^b$, $R^c$, $R^d$, $R^e$, $R^f$, and $R^g$ are as defined above.

Also in accordance with this embodiment of the invention, [Cat$^+$] may preferably comprise a saturated heterocyclic cation selected from:

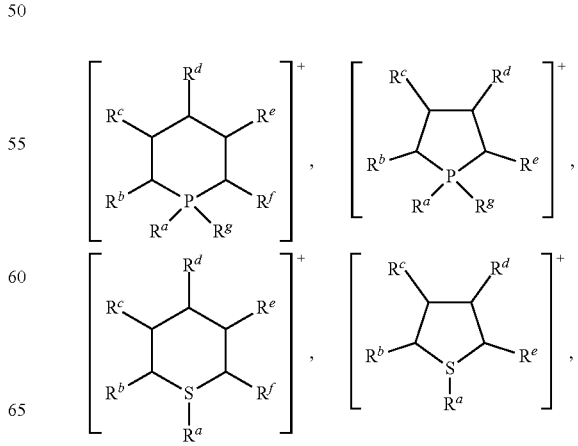

-continued

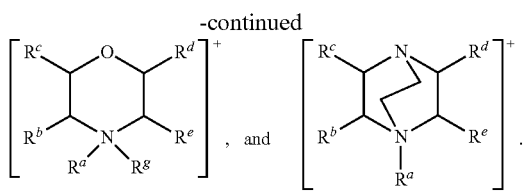

wherein: $R^a$, $R^b$, $R^c$, $R^d$, $R^e$, $R^f$, and $R^g$ are as defined above.

In the saturated heterocyclic cations above, $R^a$ is preferably selected from $C_1$ to $C_{30}$, linear or branched, alkyl, more preferably $C_2$ to $C_{20}$ linear or branched alkyl, still more preferably, $C_2$ to $C_{10}$ linear or branched alkyl, and most preferably $C_4$ to $C_8$ linear or branched alkyl. Further examples include wherein $R^a$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the saturated heterocyclic cations comprising an $R^g$ group, $R^g$ is preferably selected from $C_1$ to $C_{10}$ linear or branched alkyl, more preferably, $C_1$ to $C_5$ linear or branched alkyl, and most preferably $R^g$ is a methyl group.

In the saturated heterocyclic cations comprising both an $R^a$ and an $R^g$ group, $R^a$ and $R^g$ are each preferably independently selected from $C_1$ to $C_{30}$, linear or branched, alkyl, and one of $R^a$ and $R^g$ may also be hydrogen. More preferably, one of $R^a$ and $R^g$ may be selected from $C_2$ to $C_{20}$ linear or branched alkyl, still more preferably, $C_2$ to $C_{10}$ linear or branched alkyl, and most preferably $C_4$ to $C_8$ linear or branched alkyl, and the other one of $R^a$ and $R^g$ may be selected from $C_1$ to $C_{10}$ linear or branched alkyl, more preferably, $C_1$ to $C_5$ linear or branched alkyl, and most preferably a methyl group. In a further preferred embodiment, $R^a$ and $R^g$ may each be independently selected, where present, from $C_1$ to $C_{30}$ linear or branched alkyl and $C_1$ to $C_{15}$ alkoxyalkyl.

In further preferred embodiments, $R^b$, $R^c$, $R^d$, $R^e$, and $R^f$ are independently selected from hydrogen and $C_1$ to $C_5$ linear or branched alkyl, and more preferably $R^b$, $R^c$, $R^d$, $R^e$, and $R^f$ are hydrogen.

In accordance with the present invention, [X$^-$] represents one or more basic anionic species. The term "basic" refers to Brønsted bases having the ability to react with (neutralise) acids to form salts. [X$^-$] may comprise one more basic anions selected from alkylcarbonate, hydrogen carbonate, carbonate, hydroxide, alkoxide, chloride, bromide, nitrate and sulphate.

In preferred embodiments, [X$^-$] is selected from alkylcarbonate, alkoxide, hydrogen carbonate and carbonate. More preferably, [X$^-$] is selected from alkylcarbonate. Most preferably, [X$^-$] is [MeCO$_3$]$^-$.

A particularly preferred ionic liquid transesterification catalyst for use in the present invention corresponds to [N$_{2221}$][MeCO$_3$]. This transesterification catalyst has been found to give particularly good glycerol conversion and glycerol carbonate yield/selectivity in the process of the present invention.

In another aspect, the present invention provides a process for preparing glycerol carbonate comprising the steps of:
(i) reacting a glycerol reactant stream with: a) a dialkyl carbonate reactant stream; and/or b) a cyclic alkylene carbonate reactant stream, in a reactor in the presence of a homogeneous transesterification catalyst; and
(ii) obtaining a glycerol carbonate product stream;
wherein the homogeneous transesterification catalyst is an ionic liquid which is [N$_{2221}$][MeCO$_3$]. As will be appreciated, any preferred embodiments relating to the nature and processing of reactant and product streams described hereinbefore apply equally to this aspect of the invention.

Other suitable homogeneous transesterification catalysts include acyclic organic amines (i.e. primary, secondary or tertiary amines), as well as cyclic amines (aliphatic or aromatic), which are capable of performing that function. It will be appreciated by the skilled person that the presence of amines in the reaction mixture increases the possibility for undesired side reactions, such as alkylation by dialkyl carbonate. Nevertheless, side reactions of this nature are minimised where sterically hindered aliphatic amines and/or tertiary amines/aromatic amines are utilised. Reference to "sterically hindered" aliphatic amines herein is intended to mean either: i) an acyclic amine in which the nitrogen atom is bonded directly, or via a single carbon atom linker, to an iso-propyl, a tert-butyl group or a cyclic, aromatic or heterocyclic group; or ii) a cyclic amine in which the nitrogen atom on the ring is adjacent to at least one carbon ring atom having two $C_1$-$C_6$ alkyl substituents, preferably wherein the nitrogen atom is also adjacent a second carbon ring atom having one or two $C_1$-$C_6$ alkyl substituents.

Examples of organic amines include tert-butylamine, isopropylamine, triethylamine, ditertbutylamine, diisopropylamine, diisopropylethylamine, dicyclohexylamine, dibenzylamine, benzyldimethylamine, diacetylchlorobenzylamine, dimethylphenethylamine, 1-dimethylamino-2-phenylpropane, N,N,N'-tritert-butylpropanediamine.

Examples of cyclic amines include pyridine, pyrrole, pyrrolidine, piperidine, imidazole, and $C_1$-$C_4$alkyl-substituted derivatives thereof. Preferred sterically hindered cyclic amines include substituted piperidine derivatives having two to six $C_1$-$C_4$ alkyl substituents, preferably two to four $C_1$-$C_4$ alkyl substituents, where at least two alkyl substituents are located on carbon atom(s) adjacent the nitrogen atom of the ring. Preferred $C_1$-$C_3$alkyl-substituted piperidines include 1,2,6-trimethylpiperidine, 2,2,6-trimethylpiperidine, 2,2,6,6-tetramethylpiperidine, 2,2,4,6-tetramethylpiperidine, 2,2,6,6-N-pentamethylpiperidine.

A particularly preferred cyclic amine compound for use as a transesterification catalyst in accordance with the present invention is 2,2,4,6-tetramethylpiperidine (TMDH-piperidine, CAS #6292-82-6):

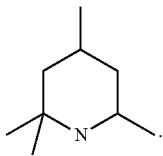

The above sterically hindered substituted piperidines, particularly TMDH-piperidine, have unexpectedly been found to give particularly good glycerol conversion and glycerol carbonate yield/selectivity in the process of the present invention and also exhibit excellent stability. These properties are also believed to be improved over conventional homogeneous transesterification catalysts known from the prior art.

In another aspect, the present invention provides a process for preparing glycerol carbonate comprising the steps of:

(i) reacting a glycerol reactant stream with: a) a dialkyl carbonate reactant stream; and/or b) a cyclic alkylene carbonate reactant stream, in a reactor in the presence of a homogeneous transesterification catalyst; and (ii) obtaining a glycerol carbonate product stream;

wherein the homogeneous transesterification catalyst is a substituted piperidine derivative having two to six $C_1$-$C_4$ alkyl substituents wherein at least two of the alkyl substituents are located on carbon atom(s) adjacent the nitrogen atom of the ring. Preferably, the homogeneous transesterification catalyst is selected from 1,2,6-trimethylpiperidine, 2,2,6-trimethylpiperidine, 2,2,6,6-tetramethylpiperidine, 2,2,4,6-tetramethylpiperidine and 2,2,6,6-N-pentamethylpiperidine. Most preferably, the homogeneous transesterification catalyst is 2,2,4,6-tetramethylpiperidine (TMDH-piperidine, CAS #6292-82-6).

As will be appreciated, any preferred embodiments relating to the nature and processing of reactant and product streams described hereinbefore apply equally to this aspect of the invention.

Figure 2:
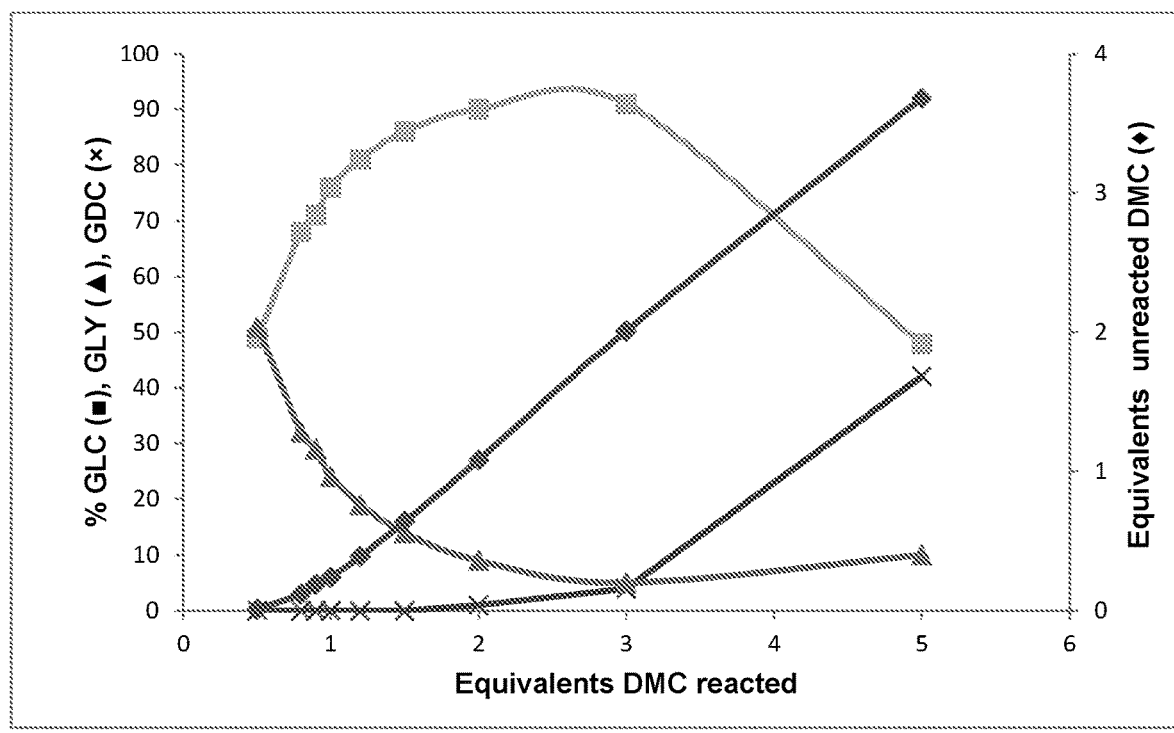
Figure 3:
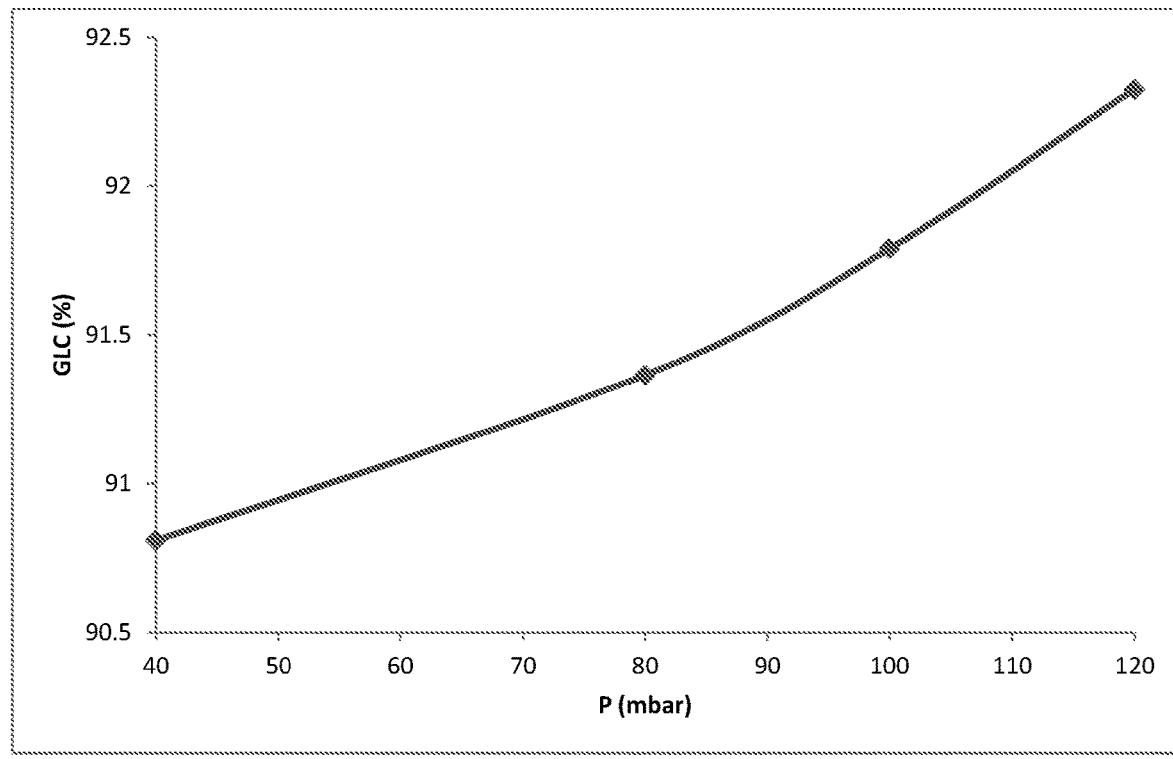
Figure 4A:
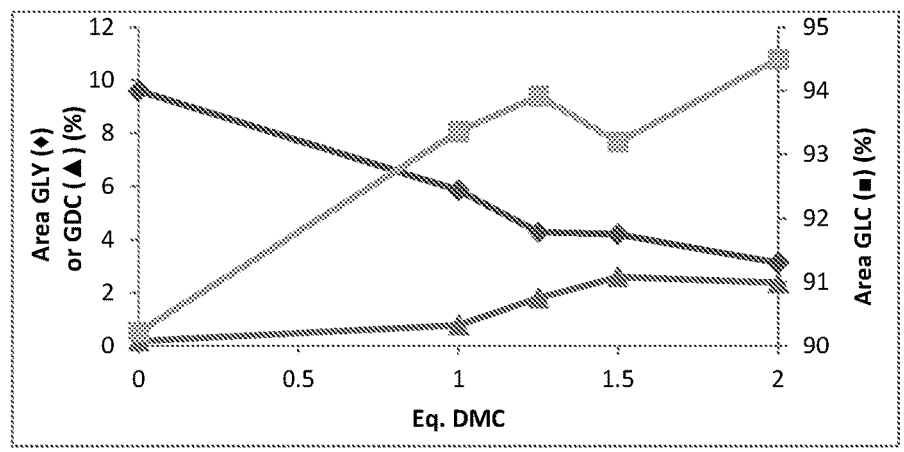
Figure 4B:
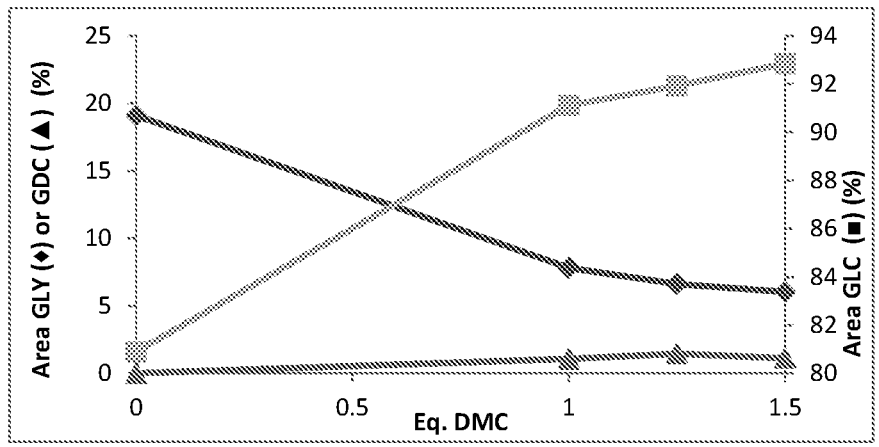
Figure 4C:
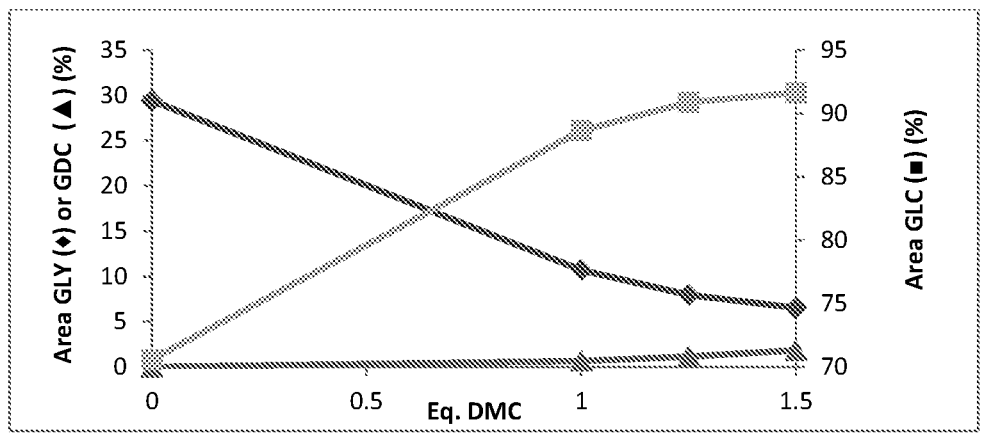
Figure 4D:
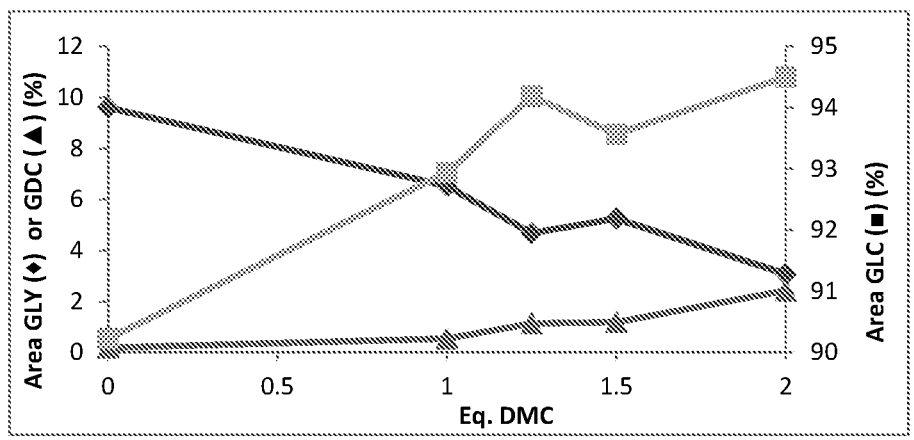
Figure 4E:
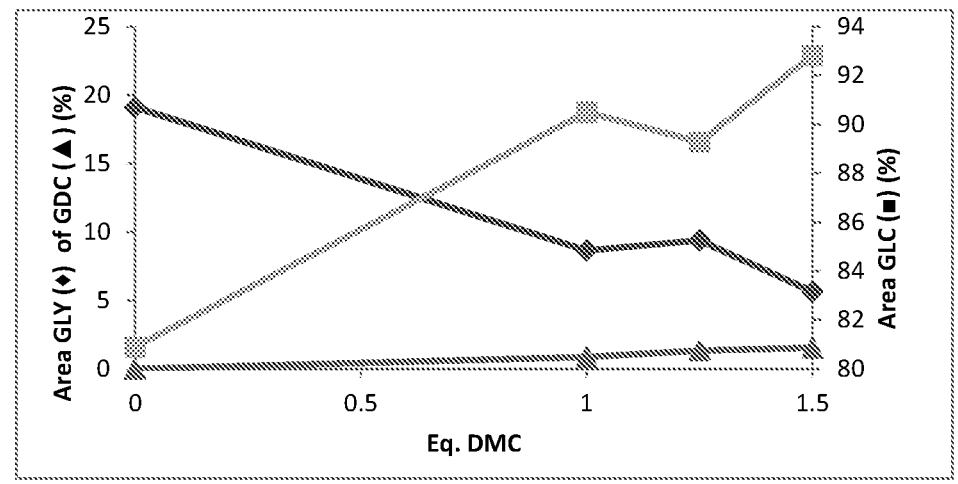
Figure 4F:
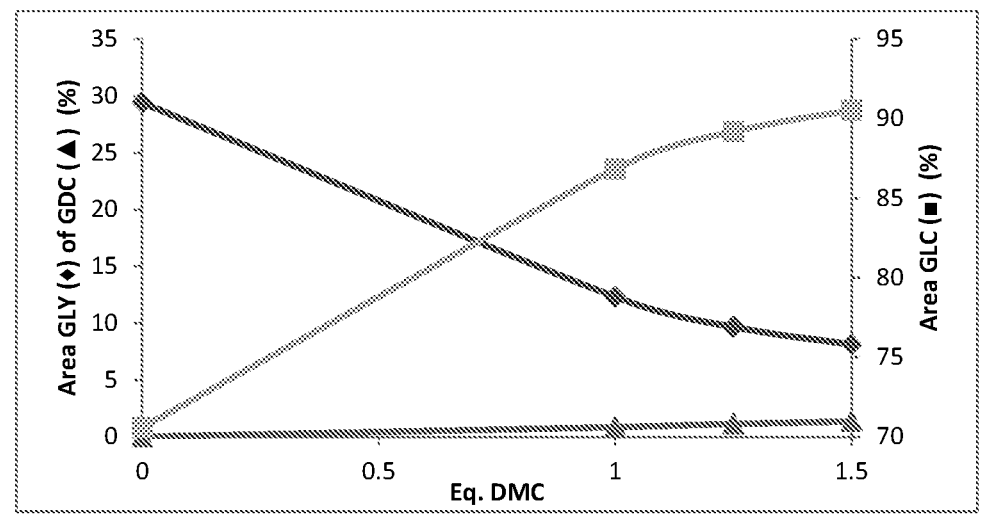

The invention will now be described with reference to the following Examples and Figures wherein:

FIG. 1: is a schematic diagram illustrating a preferred embodiment of the process of the present invention employing two separate reactors;

FIG. 2: shows a plot of reactant and product composition and the effect of dimethyl carbonate ratio and reactant/product distribution;

FIG. 3: shows a plot of glycerol carbonate % in the final product obtained following by-product alcohol removal step (ii) and subsequent reaction in step (iii); and FIGS. 4a to 4f: show plots of glycerol carbonate yield (%) for each of the samples taken from Streams A to F respectively against the number of equivalents of dimethyl carbonate present relative to unreacted glycerol at the start of each second stage reaction.

With reference to FIG. 1, a dimethyl carbonate (DMC) reactant stream (1) is fed to a mixing vessel (101). A glycerol (GLY) reactant stream (2) is also fed to mixing chamber (101). Preferably, as illustrated in FIG. 1, the glycerol reactant (GLY) stream (2) is dosed with transesterification catalyst (CAT), prior to combining with dimethyl carbonate in the mixing vessel (101). A mixed reactant stream (3) is withdrawn from mixing vessel (101) before being fed to the reaction zone of the first reactor (R1). The first reactor (R1) operates at above ambient temperature and the glycerol (GLY) and dimethyl carbonate (DMC) reactants are partially reacted therein. Typically, this stage of the process can achieve no more than 90% conversion of glycerol (GLY) to glycerol carbonate (GLC), but with near 100% selectivity for glycerol carbonate (GLC) product.

Following the incomplete or partial reaction in the first reactor (R1), a by-product methanol removal step is undertaken. A stream (4) comprising the reaction mixture is withdrawn from the first reactor (R1) and fed to column (102) for separation. Column (102) may, for example, be a distillation column or flash column. An overhead methanol (MeOH) rich stream (5) is withdrawn from column (102). Separated methanol (MeOH) rich stream (5) typically comprises an azeotropic mixture of methanol (MeOH) and dimethyl carbonate reactant (DMC). The azeotropic mixture may be separated in a subsequent step so as to provide a dimethyl carbonate (DMC) recycle stream.

The bottoms product of column (102), comprising the remaining components of the reaction mixture, is withdrawn as stream (6). If necessary, and depending on the dimethyl carbonate (DMC) content of the azeotropic mixture withdrawn from the top of column (102) as stream (5), additional dimethyl carbonate reactant (DMC) may be added by means of stream (7) to replenish dimethyl carbonate (DMC) lost in the methanol (MeOH) separation step. Stream (8) may therefore comprise a mixture of glycerol carbonate product (GLC), unreacted glycerol (GLY), homogeneous transesterification catalyst and a replenished amount of dimethyl carbonate (DMC).

Stream (8) is fed to the reaction zone of the second reactor (R2) where the second stage of reaction occurs. (R2) operates at above ambient temperature and unreacted glycerol (GLY) and dimethyl carbonate (DMC) reactants are reacted therein. Preferably, as illustrated in FIG. 1, reactor (R2) is a reactive distillation column having the capability for continuous by-product methanol (MeOH) removal, which is withdrawn from the column as stream (9). Methanol (MeOH), or a methanol (MeOH) and dimethyl carbonate (DMC) azeotrope, removed in stream (9) may be combined with stream (5) withdrawn from the column (102) as part of the methanol removal step and preferably fed to the same separation step for obtaining a dimethyl carbonate (DMC) recycle stream. Further reaction in reactor (2) advantageously provides further conversion of unreacted glycerol. By employing a reactive distillation column as reactor (R2) and ensuring continuous by-product methanol (MeOH) removal, selectivity for glycerol carbonate (GLC) is enhanced by modifying the dynamic chemical equilibrium to favour the formation of that product over by-products such as glycerol dicarbonate (GDC).

A glycerol carbonate (GLC) product mixture comprising glycerol carbonate (GLC), homogeneous transesterification catalyst, and any unreacted reactants and/or by-product methanol is withdrawn from reactor (2) as stream (10). As illustrated in FIG. 1, this stream is preferably fed to a transesterification catalyst removal unit (103), which is preferably in the form of a column packed with cation exchange resin. Stream (11) is withdrawn from the column, having had the transesterification catalyst removed from the mixture, before preferably being fed to column (104) where any unreacted dimethyl carbonate (DMC) and by-product methanol may be separated from the product mixture. Like column (102), column (104) may, for example, be a distillation column or flash column.

Unreacted dimethyl carbonate (DMC) and/or an azeotropic mixture of unreacted dimethyl carbonate (DMC) and any remaining by-product methanol (MeOH) are removed as stream (12). Any azeotropic mixture of methanol (MeOH) and dimethyl carbonate (DMC) which may be obtained in stream (12) may be combined with stream (5) withdrawn from the column (102) and/or stream (9) withdrawn from the second reactor (R2) as part of the methanol removal step and preferably fed to the same separation step for obtaining a dimethyl carbonate (DMC) recycle stream. As illustrated in FIG. 1, streams (5), (9) and (12) are fed to separation unit (105), which may, for instance, be an extractive distillation column or a column configured for pressure swing distillation.

Where the second reactor (R2) is a reactive distillation column, an additional step of separating unreacted dimethyl carbonate and/or methanol by-product from the glycerol carbonate product stream by means of column (104) is not typically necessary since it is expected that all unreacted dimethyl carbonate and methanol by-product will instead have been separated from the glycerol carbonate product during the reactive distillation. Thus, in that case, column (104) will be absent from the apparatus and stream (9) will instead comprise all of the residual dimethyl carbonate and by-product methanol.

Following separation of methanol (MeOH) and dimethyl carbonate (DMC) from the azeotrope in separation unit (105), a dimethyl carbonate (DMC) recycle stream (14) is withdrawn from the separation unit (105) as well as a methanol stream (15). Dimethyl carbonate (DMC) recycle stream (14) may be used to supply dimethyl carbonate (DMC) to stream (1) or mixing vessel (101). Additionally or alternatively, dimethyl carbonate recycle stream (14) may supply dimethyl carbonate (DMC) stream (7) which is used to replenish dimethyl carbonate (DMC) levels for the second stage reaction in the second reactor (R2). The bottoms product of column (104) is withdrawn as stream (13), corresponding to a purified glycerol carbonate (GLC) stream.

EXAMPLES

Stream Analysis

The various reactant and product streams of the examples below were analysed by HPLC analysis using a refractive index detector. The stationary phase used for the HPLC was an organic acids column (Phenomenex Rezex ROA—Organic Acids H+), the mobile phase was 7.5% acetonitrile, 0.5 mM aqueous $H_2SO_4$ and ethylene glycol was employed as an internal standard.

Example 1

First Reaction Stage Prior to Intermediate Alcohol Separation

Several reactions of dimethyl carbonate with glycerol were investigated employing 1 wt % of NaOMe homogeneous transesterification catalyst and a reaction time of 1 hour at 80° C. Different ratios of dimethyl carbonate to glycerol (from 0.5:1 to 5:1) were employed in different reactions. Following HPLC analysis of the reaction mixture composition after this reaction time, the results were used to prepare a graph (FIG. 2) showing the effect of the number of equivalents of dimethyl carbonate (DMC) to glycerol reacted.

FIG. 2 corresponds to a graphical representation showing the relative proportions of glycerol carbonate (GLC), glycerol dicarbonate (GDC) and glycerol (GLY) against the number of equivalents of dimethyl carbonate reacted. The results demonstrate that lower dimethyl carbonate (DMC) to glycerol (GLY) ratios lead to less unreacted dimethyl carbonate (DMC) at the end of the reaction for optional recycle. The results also show that as the dimethyl carbonate to glycerol ratio is increased, the proportion of glycerol dicarbonate (GDC) produced also increases. Up to a point, increasing the dimethyl carbonate to glycerol ratio increases the amount of glycerol carbonate obtained within the reaction time, up to a maximum amount of approximately 90 mol %, based on the mass of glycerol (GLY), glycerol carbonate (GLC) and glycerol dicarbonate (GDC). However, beyond that point further increases in dimethyl carbonate to glycerol ratio leads to a preference for undesired glycerol dicarbonate formation.

Example 2

First Reaction Stage Followed by Intermediate Alcohol Separation Step

In a first reaction stage, a 1:1 molar ratio of dimethyl carbonate to glycerol were reacted, with 1 wt. % NaOMe homogeneous transesterification catalyst based on the amount of glycerol fed to the reactor being dissolved in a glycerol reactant stream prior to reaction. The reactor was operated at 80° C. for 1 hour before the reaction mixture was withdrawn and fed to a distillation column for methanol separation. Several methanol separations were completed for different samples taken from the first reaction stage using a distillation column operating at a temperature of 40° C. but at different pressures (ranging from 40 to 120 mbar). Yield of glycerol carbonate following the methanol separation was determined by HPLC.

FIG. 3 corresponds to a graphical representation showing glycerol carbonate yield (%) (which also corresponds to the molar proportion relative to glycerol in this case as 100% selectivity was observed) for each sample against the operating pressure of the distillation column. The results demonstrate that, across the range of pressure investigated, increasing the pressure in the distillation column led to greater yield of glycerol carbonate (GLC) prior to further reaction in a second reactor. This trend may be observed up until the maximum practical pressure is implemented for the particular distillation temperature of the distillation column. Thus, where a higher distillation temperature is implemented, a similar trend in glycerol carbonate yield would be observed, but for a range of commensurately higher distillation pressures.

Example 3

Second Stage Reaction (without Continuous By-Product Alcohol Removal)

Various reactant stream compositions representative of partially reacted streams were tested to determine the effect of the second reaction stage. Each of the streams included a particular molar ratio of glycerol carbonate (GLC) to unreacted glycerol (GLY), as indicated in Table 1 below, and 1 wt. % of a homogeneous transesterification catalysts, based on the amount of unreacted glycerol prior to the second stage reaction.

TABLE 1

| Stream | Molar ratio of GLC:GLY | Transesterfication catalyst |
| --- | --- | --- |
| A | 90:10 | NaOMe |
| B | 80:20 | NaOMe |
| C | 70:30 | NaOMe |
| D | 90:10 | TMDH-piperidine |
| E | 80:20 | TMDH-piperidine |
| F | 70:30 | TMDH-piperidine |

Samples of each of the streams A to F were reacted at 100° C. in a round bottomed flask reactor with various equivalents of dimethyl carbonate, relative to the amount of unreacted glycerol initially present in the sample, for 2 hours in each case to ensure the equilibrium point was reached.

FIGS. 4a to 4f correspond to graphical representations showing glycerol carbonate yield (%) for each of the samples taken from streams A to F respectively against the number of equivalents of dimethyl carbonate present relative to unreacted glycerol at the start of each reaction. FIGS. 4a to 4f also show the relative proportion of glycerol (GLY) and glycerol dicarbonate (GDC) present following the reaction for each sample. FIGS. 4a to 4f consistently show that by increasing the number of equivalents of dimethyl carbonate present, glycerol conversion to product is generally increased. However, as the number of equivalents of dimethyl carbonate is increased, selectivity for unwanted glycerol dicarbonate by-product also increases.

Example 4

Second Stage Reaction (with Continuous By-Product Alcohol Removal)

A sample from the second stage reaction of Stream A experiment from Example 3 which had been reacted for 2 hours at 100° C. with 1.5 equivalents of dimethyl carbonate was taken and its product distribution analysed before it was subjected to further reaction by heating together with continuous by-product methanol removal (an open reactor vessel being used allowing volatile components to evaporate) Following the further reaction, the product distribution was also analysed at that stage. Results from the analysis conducted in respect of the sample taken from the second stage, before and after further reaction with continuous methanol removal are provided in Table 2 below. Results correspond to the relative proportions of glycerol, glycerol carbonate and glycerol dicarbonate present in the mixture tested.

TABLE 2

| Component | Product Stream of Reactor Stage 1 | Product Stream of Reactor Stage 2 (without continuous alcohol removal) | Sample from Product Stream of Reactor Stage 2 further reacted with continuous alcohol removal |
|---|---|---|---|
| Glycerol Carbonate | 90.0% | 93.5% | 97.5% |
| Glycerol | 10.0% | 4.0% | 2.5% |
| Glycerol Dicarbonate | — | 2.5% | — |

The results of Table 2 demonstrate that the composition of the feed to the second stage reactor, comprising a 90:10 ratio of glycerol carbonate to unreacted glycerol (and no glycerol dicarbonate), was changed as a result of reaction in the second stage. In particular, further glycerol conversion to product was observed. However, as can be seen from the results for the product stream of Reactor Stage 2, selectivity for glycerol carbonate for this stage of the reaction was comparable to the selectivity for glycerol dicarbonate. However, further reaction of that sample in a reactor configured for continuous by-product methanol significantly modifies the product distribution. In addition to further glycerol conversion, the further reaction of the second stage sample effectively converts glycerol dicarbonate by-product present in the composition to the desired glycerol carbonate product. A comparable product distribution is also obtained if Reactor Stage 2 is instead operated with continuous alcohol removal initially. This experiment demonstrates that incorporating continuous by-product methanol removal into the second stage of the reaction surprisingly enhances both glycerol conversion as well as selectivity for glycerol carbonate formation over glycerol dicarbonate.

The invention claimed is:

1. A process for preparing glycerol carbonate comprising the steps of:
   (i) in a first reaction zone in the presence of a homogeneous transesterification catalyst, contacting and partially reacting a glycerol reactant stream with at least one member of a group consisting of: a) a dialkyl carbonate reactant stream, comprising greater than 80 wt. % dialkyl carbonate, and b) a cyclic alkylene carbonate reactant stream, comprising greater than 80 wt. % cyclic alkylene carbonate;
   (ii) separating at least a portion of the alcohol by-product formed from the reaction in step (i) from the reaction mixture so as to obtain an alcohol-containing by-product stream;
   (iii) reacting at least a portion of the remaining reactants in a second reaction zone in the presence of the homogeneous transesterification catalyst; and
   (iv) obtaining a glycerol carbonate product stream.

2. The process according to claim 1, wherein the glycerol reactant stream is combined with the homogeneous transesterification catalyst prior to being fed to the first reaction zone.

3. The process according to claim 1, wherein the homogeneous transesterification catalyst is present in the reaction mixture in an amount from at least one member of a group consisting of: 0.25 to 5 wt % based on the mass of glycerol fed to the first reaction zone, and from 0.5 to 1.5 wt %, based on the mass of glycerol fed to the first reaction zone.

4. The process according to claim 1, wherein contacting and reacting in step (i) achieves at least one member of a group consisting of: from 50 to 90% glycerol conversion, from 70 to 90% glycerol conversion, from 80 to 90% glycerol conversion, greater than 50 wt. % of the alcohol by-product is removed in step (ii), greater than 75 wt. % of the alcohol by-product is removed in step (ii), and greater than 95 wt. % of the alcohol by-product is removed in step (ii).

5. The process according to claim 1, wherein the molar ratio of dialkyl carbonate and/or cyclic alkylene carbonate to glycerol fed to the first reaction zone is in the range of 1:1 to 3:1, 1:1 to 2.0:1, or in the range of 1.1:1 to 1.4:1.

6. The process according to claim 1, wherein:
   a) at least one of the first and second reaction zones are operated at a temperature from at least one member of a group consisting of: 40 to 160° C., 60 to 140° C., and 80 to 120° C.;
   b) the first reaction zone is operated at a pressure of at least one member of a group consisting of: from 10 kPa absolute to 1,500 kPa absolute (0.1 to 15 bar absolute), from 100 kPa absolute to 1,000 kPa absolute (1 to 10 bar absolute), and from 200 kPa absolute to 600 kPa (2 to 6 bar absolute); or
   c) the second reaction zone is operated at a pressure of at least one member of a group consisting of: from 5 kPa absolute to 150 kPa absolute (0.05 to 1.5 bar absolute), from 10 kPa absolute to 100 kPa absolute (0.1 to 1 bar absolute), and from 15 kPa absolute to 50 kPa absolute (0.15 to 0.5 bar absolute).

7. The process according to claim 1, further comprising a step of introducing at least one member of a group consisting of: further dialkyl carbonate for reaction in the second reaction zone to replenish dialkyl carbonate lost during alcohol separation step (ii) and further cyclic alkylene carbonate for reaction in the second reaction zone to replenish cyclic alkylene carbonate lost during alcohol separation step (ii).

8. The process according to claim 7, further comprising the condition selected from at least one member of a group consisting of: the molar ratio of dialkyl carbonate is higher in the second reaction zone than in the first reaction zone and cyclic alkylene carbonate to glycerol is higher in the second reaction zone than in the first reaction zone.

9. The process according to claim 1, wherein the process comprises continuous removal of alcohol by-product as it is formed in the second reaction zone.

10. The process according to claim 1, comprising at least one of:
   a) the dialkyl carbonate reactant stream comprises:
      i) greater than 90 wt. % dialkyl carbonate;
      ii) less than 5 wt. % alcohol; and
      iii) less than 2 wt. % water; and
   b) the cyclic alkylene carbonate reactant stream comprises:
      i) greater than 90 wt. % cyclic alkylene carbonate;
      ii) less than 5 wt. % alcohol; and
      iii) less than 2 wt. % water.

11. The process according to claim 1, wherein the process further comprises a step of recovering the homogeneous transesterification catalyst from the glycerol carbonate product stream using a cation exchange resin.

12. The process according to claim 1, wherein a stream comprising an azeotropic mixture of dialkyl carbonate reactant/cyclic alkylene carbonate and by-product alcohol is obtained as a result of the process; wherein the process further comprises a step of separating the unreacted dialkyl carbonate/cyclic alkylene carbonate from the azeotropic mixture to form a dialkyl carbonate/cyclic alkylene carbonate recycle steam; and wherein the dialkyl carbonate/cyclic alkylene carbonate recycle stream is used as a source of dialkyl carbonate/cyclic alkylene carbonate reactant for the process.

13. The process according to claim 1, further comprising at least one of:
   a) a dialkyl carbonate reactant stream is employed in the process, wherein the dialkyl carbonate reactant is selected from dimethyl carbonate, diethyl carbonate or mixtures thereof; and
   b) a cyclic alkylene carbonate reactant stream is employed in the process, wherein the cyclic alkylene carbonate is of Formula I below:

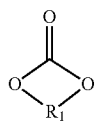

(I)

wherein:
   $R_1$ is a divalent group, —$(CH_2)_n$—, wherein n is an integer of from 2 to 6, and which is unsubstituted or substituted by at least one $C_1$ to $C_6$ alkyl group.

14. The process according to claim 1, wherein the homogeneous transesterification catalyst is selected from alkali metal carbonate, alkali metal bicarbonate, alkali metal hydroxide, alkali metal oxide, alkali metal alkoxide, alkali metal aluminate, alkali metal silicate alkaline earth metal carbonate, alkaline earth metal bicarbonate, alkaline earth metal hydroxide, alkaline earth metal oxide, alkaline earth metal alkoxide, alkaline earth metal aluminate, alkaline earth metal silicate or combinations thereof.

15. The process according to claim 14, wherein the homogeneous transesterification catalyst is selected from NaOMe, CaO, $NaAlO_2$, $Na_2SiO_3$ or combinations thereof.

16. The process according to claim 1, wherein the homogeneous transesterification catalyst is a basic ionic liquid of the formula:

[Cat$^+$][X$^-$]

wherein: [Cat$^+$] represents one or more cationic species; and
[X$^-$] represents one or more basic anionic species;
wherein: [Cat$^+$] comprises:
   a) an acyclic cation selected from:

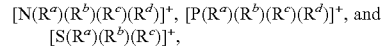

wherein: $R^a$, $R^b$, $R^c$, and $R^d$ are each independently selected from a $C_1$ to $C_{30}$, straight chain or branched alkyl group, a $C_3$ to $C_8$ cycloalkyl group, or a $C_6$ to $C_{10}$ aryl group; and wherein said alkyl, cycloalkyl or aryl groups are unsubstituted or may be substituted by one to three groups selected from: $C_1$ to $C_6$ alkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —$NO_2$, —C(S)$R^x$, —$CS_2R^x$, —SC(S) $R^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S ($C_1$ to $C_6$alkyl), —$NR^yR^z$, or a heterocyclic group, wherein $R^x$, $R^y$ and $R^z$ are independently selected from hydrogen or $C_1$ to $C_6$ alkyl;
or
   b) an aromatic heterocyclic cationic species selected from: benzimidazolium, benzofuranium, benzothiophenium, benzotriazolium, diazabicyclodecenium, diazabicyclononenium, diazabicyclo-undecenium, dithiazolium, imidazolium, indazolium, indolinium, indolium, oxazinium, oxazolium, iso-oxazolium, oxathiazolium, phthalazinium, pyrazinium, pyrazolium, pyridazinium, pyridinium, pyrimidinium, quinazolinium, quinolinium, iso-quinolinium, quinoxalinium, tetrazolium, thiadiazolium, iso-thiadiazolium, thiazinium, thiazolium, iso-thiazolium, triazinium, triazolium, and iso-triazolium;
and wherein: [X$^-$] comprises an anion selected from alkyl carbonate, hydrogen carbonate, carbonate, hydroxide, alkoxide, chloride, bromide, nitrate and sulphate.

17. The process according to according to claim 16, further comprising at least one of:
[Cat$^+$] comprises a cation selected from:

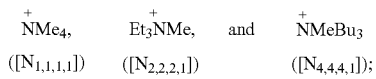

and
[X$^-$] comprises an anion selected from alkyl carbonate.

18. The process according to claim 17, wherein [X$^-$] comprises an anion selected from [MeCO$_3$]$^-$.

19. The process according to claim 1, wherein the homogeneous transesterification catalyst is:
   a) an organic acyclic amine selected from tert-butylamine, isopropylamine, triethylamine, ditertbutylamine, diisopropylamine, diisopropylethylamine, dicyclohexylamine, dibenzylamine, benzyldimethylamine, diacetylchlorobenzylamine, dimethylphenethylamine, 1-dimethylamino-2-phenylpropane and N,N,N'-tritertbutylpropanediamine; or
   b) a substituted piperidine derivative having two to six $C_1$-$C_4$ alkyl substituents and where at least two of the alkyl substituents are located on carbon atom(s) adjacent the nitrogen atom of the ring.

20. The process according to claim 19, wherein the homogeneous transesterification catalyst is selected from 1,2,6-trimethylpiperidine, 2,2,6-trimethylpiperidine, 2,2,6,6-tetramethylpiperidine, 2,2,4,6-tetramethylpiperidine, 2,2,6,6-N-pentamethylpiperidine.

* * * * *